United States Patent [19]
Goldberg et al.

[11] Patent Number: 5,441,885
[45] Date of Patent: Aug. 15, 1995

[54] BACTERIAL STRAINS FOR BIOREMEDIATION

[75] Inventors: Ina Goldberg, Basking Ridge; Paul Allenza, Flemington, both of N.J.; Francis S. Lupton, Evanston, Ill.

[73] Assignee: AlliedSignal Inc., Morris Township, Morris County, N.J.

[21] Appl. No.: 148,122

[22] Filed: Nov. 5, 1993

Related U.S. Application Data

[63] Continuation-in-part of Ser. No. 49,281, Apr. 13, 1993, abandoned.

[51] Int. Cl.$^6$ .................. C12N 1/21; C12N 15/03; C12N 15/23; C12N 15/74
[52] U.S. Cl. .................. 435/252.34; 435/172.3; 435/320.1; 435/252.3; 435/189; 536/23.2
[58] Field of Search ............... 435/320.1, 252.3, 172.3, 435/91.1, 91.32, 91.4, 91.41, 91.51, 189, 248, 252.34, 874, 877, 875; 930/240; 935/14, 29, 38, 56, 60, 72; 536/23.1, 23.2, 24.2

[56] References Cited

FOREIGN PATENT DOCUMENTS

WO90/10601  3/1989  WIPO .

OTHER PUBLICATIONS

Ruger et al. 1983. Int'l. J. Syst. Bacteriol. 33, 85–89.
Lesk, A. M. (ed.). 1988. in: *Computational Molecular Biology. Sources and Methods for Sequence Analysis*, Oxford Univ. Proc., Oxford., pp. 161–163.
Reek et al. 1987. Cell. 50, 667.
Lewin, R. 1987. Science 237, 1570.
Watson, J. D. 1987 in: *Molecular Biology of the Gene.*, 3rd edition. Benjamin/Cummings Publ. Co., Menlo Park, Calif. p. 313.
Tokuyama et al., Japan, Fermentation Eng. vol. 66, No. 2, pp. 103–107, 1988 "Cloning and expression of the hydroxylamine oxidase gene of *Nitrosomonas europaea* in Pseudomonas
Hooper, Univ. of Minnesota, Biochemistry of the Nitrifying Lithoauthotrophic Bacteria, pp. 239–265.
Wood, P. M. 1986, "Nitrification as a bacterial energy source" pp. 39–62, in Prosser, J. I. (editor) Nitrification, Special Publications of the Society for General Microbiology, vol. 20, IRL Press, Oxford.
McTavish, H. E. "Enzymology and Molecular Biology of Ammonia Oxidation in *Nitrosomonas europaea*" Thesis for Doctor of Philosophy, Nov., 1992.
Mellor et al. "Reduction of nitrate and nitrite in water by immobilized enzymes" Nature, vol. 355, 20 Feb., 1992.
McTavish et al., "Sequence of the Gene Coding for Ammonia Monooxygenase in *Nitrosomonas europaea*" Jour. of Bacteriology, Apr. 1993, pp. 2436–2444.
McTavish et al., "Multiple Copies of Genes Coding for Electron Transport Proteins in the Bacterium *Nitrosomonas europaea*", Jour. of Bacteriology, Apr. 1993, pp. 2445–2447.
Ensign et al., "In Vitro Activation of Ammonia Monooxygenase from *Nitrosomonas europaea* by Copper" Jour. of Bacteriology, Apr. 1993, pp. 1971–1980.
Smith et al., "Isolation and Characterization of a Nitrite Reductase Gene and Its Use as a Probe for Denitrifying Bacteria" Applied and Environmental Microbiology, Jan. 1992, pp. 376–384.

(List continued on next page.)

*Primary Examiner*—Christopher S. F. Low
*Attorney, Agent, or Firm*—Mary Jo Boldingh; Harold N. Wells; Roger H. Criss

[57] ABSTRACT

The present invention provides a recombinant plasmid adapted for transformation of a host microorganism, the plasmid comprising a plasmid vector into which a polydeoxyribonucleotide segment that codes for ammonia monooxygenase and hydroxylamine oxidoreductase has been inserted, wherein the resulting transformant exhibits at least 50% of the overall level of ammonia monooxygenase and hydroxylamine oxidoreductase activity of the donor. Also provided are an isolated polydeoxyribonucleotide segment that encodes ammonia monooxygenase and hydroxylamine oxidoreductase, and a transformant containing the ammonia monooxygenase and hydroxylamine oxidoreductase gene segments.

16 Claims, 13 Drawing Sheets

OTHER PUBLICATIONS

Robertson et al., "Simultaneous Nitrification and Denitrification in Aerobic Chemostat Cultures of Thiosphaera pantotropha", Applied and Environmental Microbiology, No. 1988, pp. 2812–2818.

Papen et al., "Heterotrophic Nitrification by *Alcaligenes faecalis*: $NO_2-$, $NO_3-$, $N_2O$, and NO Production in Exponentially Growing Cultures", Allied and Envir. Microbiology, Aug. 1989, pp. 2068–2072.

Schmidhauser et al., "Regions of Broad-Host-Range Plasmid RK2 Involved in Replication and Stable Maintenance in Nine Species of Gram-Negative Bacteria" J. of Bacteriology, Oc. 1985, pp. 446–455.

Ullrich et al., "Human $\beta$-nerve growth factor gene sequence highly homologous to that of mouse", Nature, vol. 303 30 Jun., 1983, pp. 821–825.

Akam, "Hox and HOM: Homologous Gene Clusters in Insects and Vertebrates" Cell, vol. 57, 347–349, May 5, 1989.

```
CTGCAGGTAC GAACCCCCTT GCAGGAGCAA GACGTGATAA TCCGATGGAA  50
CAGCCAGGAC ACGACGCACA GCGGCGTCGG TACGATGGGC AAAATCCATG 100
AAAGGCTGGG AACGATGGCT GATTTCCATC ACGGACACCC CTGTGCCCGC 150
AAAATCAAGC AGCTCATCAC GTATTTGCAA TAGAACATCC ATTGGCAAGG 200
CGCTGGGCCC TGCGCTGAAA TTAAAGGGTC GGGACATACT TGCTGAGATC 250
CTGTACAAAC CTGAACGCCG GAACAGGCCC CCCTATTTCG GCAATGACAA 300
TCAAGTCTAC GAGCACAATG GTCTGATTAG TCAGACCATT AATATTCTCT 350
GGAGCAGACC GCATGACGCG TTCGTTTGAA CTGGACACCT TGAAGATGCG 400
TCTTAACGAT GACGAACTTC AATCCCTGGA TCTTCACCAG CGCATTCAGC 450
GTGCCTTGCG GGCATTGATT CTGGATGGCG CCCTGGGTCC CGGGGTCAAG 500
CTGCCTGCCA CACGCTCCCT GGCCAAATCT CTGAGCATGG CCCGCGATAC 550
GGTTGAAAAC GCCTATGTTC AGCTGCATCG CGACGGCTTT ATCGTGCGAC 600
GTGAAGGCTC AGCAGCTAT GTTTCTGAAT CGGTCGGCAC GGAGCTGCGC 650
GGCAGTGCCT ACCGTCGCAT CAAAGCCCAG GATCTGAAAC GCAGCGTGAT 700
GGAACCCGGC ACGGGTTTAA GCCGCCGGGG TCGCGCCGTG TTTGAAAGTG 750
GCGGCATTGC CGATCAACAG ACCATCAAGG CCTTTGCCAC GGGTTTGCCA 800
GAAACCCGCA ACTTCCCCAC CGATGTGTGG GAGCGCCTGC AACGTCAGGC 850
CATGAAAGAC TACCGGGCCA ACATCCTGCT GCATGGCGAC CCGCAAGGCA 900
CCGAGTCCCT GCGTAAAGCG ATTGCCGTGT ACTGAATCT GGAGCGTGGT 950
GCGAAAGTCT CTGCCGATCA AATTTTGATT CTGAGCAGCA CGCGCCAAGC 1000
CCTGTTCCTG TGTGCGCAAT GCTGGTCGA TGCTGGCAAA CCCATTCTGG 1050
TCGAGAACCC CGGCTACTTC GGCGCCCGCA AAGCCTTTGA AGCGGCCGAG 1100
GCCCGTGTGG TACCGATTGG TGTAGACGAA CAAGGTTTGC GCACCGATTT 1150
GCTCAATGAA GATCGCAGCG GCGCAAACTG TATTTATGTA ACGCCCTCGC 1200
ACCAGTATCC CACCGGGGCT ACCATGTCCC TGGAGCGTCG TCTGGAACTC 1250
ATACACTGGG CAGCAGAAAA TGGCCGCTGG ATTATGGAAG ACGACTACGA 1300
CAGCGAATTT CATTACGACG GCTACCCAC GGCATGTGTG CAAGGTCTGG 1350
ATAAATACCA GCGCACCATC TACCTGGGCA CCTTCAGCAA AACCCTGTAT 1400
CCGGGCCTGC GCATGGGCTA TATGGCCTTG CCGCCCGAGC TGGTCAAACC 1450
CTTTACCCAA GCCCGCAGCA TCATGGATGG CCATACACCG CAAATCCTGC 1500
AACTGACGCT GGCGCGCTTT ATGAAGACG GGCATTACAA CTCTCATATT 1550
CGCGCCATGC GCAAACTGTA TGCCGGGCGA CGAGAAATCA TGCTGGAAGC 1600
CATCGAGCAG CACTTGCAAG GCATAGTCCG TGCAGCTCGA CCTGAAGGTG 1650
GTTTGCAGAT TCCCTGCTTT CTGGAGCCGG GCTGGTCAGA AGAACACACG 1700
CTGCCGCCGCG CTTTGAGTGC GGGCGTTCAA CTGCCAGGTT TGAGCCGTCT 1750
GTACATTGGT GAGGAAAAAC AACAGGGCTG GTTGCTGGGC TATGCATCCC 1800
TGACCGCCTA CGAGATCGAA TCCGCCATGT TGCGTCTGGC CAACGCACTC 1850
CGCCAGGGCA AAGGCTAGGT CAGGAAAAAT CAGTACATCA AGGGGAATCG 1900
```

FIG.5a

```
CCGGTTCAAG TCGGCAACCC CTTCCAGAAT GGCATTCTCG GTGCGGGGAT 1950
TGCGCGAACC ACTGCGCACC CCGCCCAGCA AGGCCAGAAT CATGTCGCCG 2000
ATTTCCTTGA AATCGTCCTC GCCCAAACCG CGCCTGGTAC AGGCGGCGCT 2050
GCCCACACGC ACCCCCGAGT ACGCACCAGT GACCTGCTCA TAAGGCACCC 2100
GGTGCTTGCT CAAGCTAATG CCTAACTGAG CCAGAACCCG CTCCACCAAA 2150
GGCCCGGACA AGTCCCAAGG GCGCAAATCC ACCACACCAA AATGACAGTC 2200
TGTACCGCCT GATACCACTG TCAGCCCACC TTCGGCCAAA CGACGACACA 2250
AGCTGCGCGC ATTGATGATG ACGGACTGGG CATAGGCCTT ATAGGACGGA 2300
CTCATCGCCT CACCCAAGGC CACGGCCTTG GCCGCCAGAA TGTTCAGCAA 2350
AGGCCCGCCT TGCAGCCCTG GATACACCGC CTGGCTCAAG CGCTCGGCCA 2400
GCTTGGGTTC ATTGCTCAGG ATGATCCCGC CACGCGGACC GCGCAAGGTG 2450
CCATGCGTGG AGAAAGTCGT AACGTGCGCA TGCTTGACGG GCGACTCCAT 2500
CAGCCCCGCA GCAACCAGTC CCGCACTGTG CGCCAAATCC ACCATCAGGT 2550
AGGCATTGAC CTCGTTGGCG ATATTTCTGA ACTCGGCAAA ATTCGGGGTC 2600
CGTGAATAAG ACGATCCTCC GGCAATGATC AGCCGTGGTC GTTCCTTGTG 2650
AGCCAGAGCG CGGACTTCAT CCATGTCCAC CCATTGCGTC TGACGATCCA 2700
CCCCATACGA GCAGGTCTGA AACCAGCGTC CGGACACATT GAAATGCGAG 2750
CCATGGCTAA GGTGCCCACC CGGACTTTGG TCCAGCGCCA GAATCGTGTC 2800
GCCCGGTGAG AGCAAGGCCA GATACACCGC CAGATTAGCC TGACTGCCCG 2850
AGTGCGCCTG CACATTGGCA TAGGAGGCCC CAAAAACCGC CTTGGCCCGC 2900
TCGATGGCCA GCTCTTCAGT TTGATCGGCT TGTTCGCACC CGCCGTAAAT 2950
CCGTTGCCCA GGATAGCCTT GCGCCTGCTT GTTGCTGAGC AAGGAGCCCT 3000
GCACGTCCAG AACGGAGCGG CTCAGGTAAT TCTCGGAAGC GATCAGCTCA 3050
ATGGTGTGTT GTTGGCGACG CCGTTCGGCT TCGATGATGT CCCAAAGATT 3100
GCGATCGCTT TGCTGTAGAA ATTGCGAACC CACCAGAGGC AGGTGGGGGG 3150
TGTCGCCACC GGCAAGACTC TTCATGGGAG TTCCTGTTTA GAAATTGGCT 3200
ACTGTTGCCA CCGTGCAGAC TTTTCAAACA CAGGCAAAAG TGCAGCCCTG 3250
GCATGACGAT TCCAAGGGCG AAAGATAAAC ATCCTATTCT GTTTATCGAC 3300
CTATCAAACA GTCCATTAAA AATAAATCCA CCAGACCACT TTTAATTATT 3350
GTTATTTGAA TAAACATTCA AAGCATAAAG AATTAAAAAT CACCTGAAAC 3400
CAAGCTATAA AGCCAATCCC GATTATTCTT GTCAACAATT AAAACAAGAT 3450
TCAAATTTTT ATTATTAAGT GGTCTGTTAA ATAGCCGAAA AATGGTCTGT 3500
CATTTATTGT CATAGGATCA TTAGAATGCA GCCAACGAAT ACTCAAGACC 3550
CATACTTCTA AACGCTCAAG CAGATTATCA CCTTTCTCTA TCTGCGCACG 3600
ATAAAAACAT CCTCAGTTTT CCCACGACTA CAGGAAACTC CATTGCTTTA 3650
ACGGCAGTTC AACCACGCTG ATCCCCACGG TTTGAGAAAC CCGGCAACGG 3700
GATTTTTTTG GGCCTTGTCC ATAAGAATCG GCAAATCCTT TTAAGCCTGC 3750
GAATTTCCAT TTGGAAATAA AGATGGGTGG AATAAAGAAA CGACCTGTTC 3800
ATTTCGAACA GATCGCAATC AACAGCAAGG AAGTTTGAAA TGACAATCAA 3850
AAGCTACGAA ACTGATGACG CCGTACGTAA TATGCTGCAA AAGCTGTCTG 3900
```

FIG.5b

```
TACTTTGGAA AAACCGGGCT GCCGTGAATC AGGAGCTGCC GGACTACAAC 3950
AATCTGGCGT TCGATCCCAA CAAGGCTGAC TTCAGCGAAT GCCTCTTGCC 4000
GTTCCGCGAG CATCAGGCCT GGCTGGAAGC ACCTGAAGAA TTGAAATCGC 4050
AGTGCTTGTC CTACGCTTGG GGCATTTACA ACCTCAAGAC CATTTATGTT 4100
GAATGCAACG TGGTCACCCC TTCTTGCGAA GACATCATCA AGACCCCGCC 4150
CCCAAGCGCC AACCGCAATC TGCTGCAAGA TGTGATGTCC CAGGCTTTGC 4200
TGGACGAGGC CCTGCACACG CGCATGTCGA TCATGGCCTG CAACTACATC 4250
TACTCCATGC GTGGTTTGAC GCCCCTGGAT TTCACCAATT TCAACCTGGT 4300
GCAGTGGCGC AATGACATCC TGAGCCAGTG CAGCTCCGAA TCCGAGCGTC 4350
GCCTGACCCG CTTTGCCATT GCCTGCGCCT CCGAGACCCT GATTACCGAC 4400
TATCTGAAGA CCATGGCCGA GGACAAGAGC ATCCAGACCG TGTGCCATGA 4450
AGTCACCCGC ACTCACGCCA TGGACGAGTG GAGCCATTCC AGCGTGTTCA 4500
GCTTTGTGGC CTCCGACATC ATTCACGGCC TGAGCCAGAA AGAGCGCGAG 4550
CACATGCGTG CCGTGATTTT GCGCACCGTG GAAATGTTCG CCAACAATGA 4600
AATGGGTGCC TGGGAAAAGG TCTTCTCCAT GGTGAACTTC CCCAACGCTC 4650
GCGACATCTT GCACGACACC GGCGACTCCA ACGAAATTGG TGTGTACACC 4700
GGCTCGGTAG AAAGCCTGAT CGAGCGCATT GGCTTGAACA GCAAATCCGG 4750
CAAGGCCCAG CCCGAGGCCG AACAGCAGGA GGCGCTGCAA TGACAGCCAT 4800
GATTCAGGCG CGCTGCCGAGA CCGTTCGCCC CGAGGCCGGG AACGTCAAAG 4850
TGTTTACCTT GCGAGTGCAA AGTGGCCACT TTGATTTTCT GAGCGCCTTG 4900
CGGGCAGGCA AGCATGTCGC CCTGAGCTAC CCCGATACCG GCGGCACCAT 4950
TCAACAGCGT ATGTATTCGA TCACCCGTGT GGCCGATCCA GACCTGATTG 5000
AAATTGCCGT GAAAGGGTCG GGCCGCAATA GCGTCTCCGA TCATCTGCAT 5050
GCCACCTTGC GCGAGGGCAT GAGTGTGCCC CTGCAATATG TGGCGGGTGA 5100
GATCC
```

FIG.5c

```
GGATCTCGGT GGACTCGATT GTGGGTTACC AGCGTATCGC CATGATCGCC  50
GGCGGCATTG GCATTACCCT GCCCATTGCC TTGCTGCGTG AATTGGCGGC  100
GCGAGCCCAG GACGGCTTGC CTGTACCACA AGTACATTTG CTGCTCAGTA  150
TTGCCCGTAT TGCCGACATT CCTTTCCTGC ACGAGCTGCT GCAGCTGGAC  200
CTGGGCACCA GCTGGTTCAC ACTGACGGTG TTTGTCACGC AGGAAAAAAT  250
CCGCGAAAGC GCTCATTTCA AAGTGGGACG CCCCTCTTTT GAGAATATGG  300
AGCAATTGAA AGACCCGCAG GCCGTGGTGA TTTGCGGCAG CCATGGGTTT  350
GCCCAGGCCT TGCGCGAATA CACCATTCAG GCGCACCCCA TCTCGCACAT  400
GTTGATTGAA GCCTTCTCCC CACCGGCCAA AGCGGGTGTG GAAATCCTGC  450
CTGAAGCAGG CAGTGCCCCC TTGCAAATCA ATGTACGCAG CACCGGACAA  500
ACGCTCAACC CTGAGCCGGG CAGCAGCCTG CTGGAAATGC TGGAAGCAGG  550
CGATGTGCCT ATTCGCAGCC AATGCCCGTTC GGGCATTTGC GGCGCTTGCC  600
GGGTACAGAT ATCGGAGGGC GAATACCGCT CCGAACCCGA CTTTTGCCTG  650
AGTGATCAGG ACAAGCCCCA GGGCCATGCG CTGGCGTGTT GCACCTTCCC  700
CCTGTCGGGT GCCATTAATG TAGACATCGG TACCACGAGC TGACATCCTT  750
ACCATCTGAA TTGAAAGAAA CTCTTATGAA GAAAGTCATC GCACTGCGTC  800
ATATCCATTT TGAAGACTTG GGCACACTGG AACCTGTTCT GATCGAACAG  850
GGCTACCAAG TTCAATATAT TGACCCTTCC GTCGAGTCAC TACGCCATGT  900
GGGTGAACAG GACGCTGACC TGCTGGTTGT ATTGGGCGGG CCAATCGGGCG  950
CCTACGACGA AAAGATTTAC CCCTTCCTGT CCGATGAGCT GGAACTGATC 1000
AACAAGTTCT TGCTGGCAGG AAAACCCCTG CTGGGCATTT GCCTGGGCGC 1050
GCAACTGATT GCTCGTGCTC TGGGAGCCAA TGTGTATCCG CTGGGTGTGA 1100
AAGAAATCGG TTTCTCTCCC CTGAAACTGA GTGAAGCGGG CAAAGAATCG 1150
CCCCTGGCCG CCGTCAGCGG CATTCCCGTC CTGCACTGGC ACGGGGATCA 1200
GTTCGACATT CCCGATGGAG CCATTCACCT GGCCAGCACG GACGTAGGCC 1250
CCAACCAGGC CTTCTCCCTT GGAAGCCAGG TATTGGGTCT GCAATTTCAC 1300
```

FIG. 9a

| | | | |
|---|---|---|---|
| CTGGAGGCCG | ACACCAGCAA | GCTGGAACGC | TGGCTGGTTG | GTCATGCCAA | 1350 |
| CGAACTGGGA | CAAGCGGATA | TCGACCCGCA | GATGCTGCGT | CTGGAAGCCA | 1400 |
| TGGCGGTACA | AAAACGCCTG | CACGCCGCTG | CTGCTACGGT | CCTGACCAAC | 1450 |
| TGGCTCAGCC | AACTTAAACA | AGCCAGTTCC | GCTGATTGTG | CTGCATGAAC | 1500 |
| ACTGCTGTAA | CGTTTGTTGA | TCGCRAACGA | CATCCCTACC | ATGTGGATGT | 1550 |
| CGTTTCGATT | CAGTCTCAAG | TGGTCTACGG | TCGGGTGGGC | AACAATGTTG | 1600 |
| CCGGCCCGAC | CTTACGTAGG | CACGGCTTTA | AAGTCGCCGC | CGTTCCCACC | 1650 |
| GTGTTGCTCA | GCAACAACCC | GCAATACCCC | ACCGTGCACG | GCGGTGCCGT | 1700 |
| CCCGATGAA | TGGCTGAAAG | GCTTTCTGGA | TGACCTGGTG | CTGCGTGGTG | 1750 |
| CGCTGGACAA | GGTGCGCGCT | GTCCTGATCG | GTTATCTGGG | CAGCGCCAAT | 1800 |
| CAGGCCGTCA | TCATTGCGAA | CTGGCTGAAG | GCCTTGTTGC | AAGACCATCC | 1850 |
| GGACACTCTG | GTCATCGTGG | ACCCGGTCAT | AGGCGATCTG | GATGTAGGAG | 1900 |
| TCTACGTAGA | CCCGGCGCTG | ATTCCCGCCT | ATCACGAAAC | CTTGCTGCCG | 1950 |
| CTGGCCACGG | GCCTGACTCC | CAATAACTAC | GAGCTGTCCT | TGCTGTCCCA | 2000 |
| ACAGCCTTGC | GACACCATCC | AGGGCAGTTC | AAGCGCCGCG | CACGCCTTGC | 2050 |
| TAAATGGCCG | TACCGAATGG | GTCATTGCTA | CCAGCGCCGC | TCCCGACTCC | 2100 |
| TGGCAGGATG | GCCAGATCAA | ATTATTAATG | TCGCGCAAAG | AACCCCGCGC | 2150 |
| CGACACCCTG | CTTAGCCATC | CTCGCGTCGA | TTGTGCCGCC | AAAGGCACCG | 2200 |
| GCGACCTGTT | TGCCTCCACC | TTGCTGGCCC | ACCTGATTTT | GGGTGCAGAC | 2250 |
| CTGCATTCGG | CGGTGCATAC | AGCCAGTGCC | AGTGTGCTGC | TTCAATTGGA | 2300 |
| GTTGACCCGA | CAGGCCGGAC | ATCAGGAATT | AATTTTGCCG | ATAGATCCTT | 2350 |
| TCCGAGCCTG | AGCAAATATT | TCTTAATCTA | ACAAACCTTT | CAACAGGCAG | 2400 |
| TCGTTCTCGT | TAAGCTGTGC | CCTCTTAGTT | ACAAACGGAG | CATGACATGG | 2450 |
| GGCTGCCTTT | TAAAAGCACG | CTACATCCAC | GGGTGTTCTG | GGGATCTACC | 2500 |
| TTTATCGTCC | TGGTCTTTTT | GCTGATCGGG | ATTATTTTCC | CTAAAGACGC | 2550 |
| CGCACTTATT | TTTGAGCAGT | TACAAAACTG | GGTCATCAAA | AGTTTCGGCT | 2600 |
| GGTTCTATAT | CCTGGCTGTG | GCCTTGTTTT | TCTTTGCCGT | CGTCTATCTG | 2650 |
| GCATTAAGCC | GCTACGGCAA | CTTGAAATTA | .GGGCCGGACG | ACTCGGAACC | 2700 |

FIG. 9b

```
TGACTACCCG TATCTCACCT GGATGGCAAT GCTATTTGCC GCCGGTATGG 2750
GTATTGGTTT GATGTTCTTT GCCGTGCCCG AACCACTGCA ACACTTCTCG 2800
GCCCCACCCT CGGGTCTGGC CAGCACAGTG GAAGCCGCCC ATCAGGCGCA 2850
GATCATCACC TTCTTTCACT GGGGCGTTCA TGCCTGGGCC GTCTATGCGG 2900
TCGTGGGTTT GTCGCTGGCC TATTTCTGCT TTCGCTACAA CCTGCCCGTTA 2950
ACGATTCGCT CGGGCCTGTA TCCCTTATTT GGCAAGCGCA TTGAAGGCTG 3000
GATTGGCGAT AGCGTGGATA TTTTCGCCGT TTGCGGCACG CTATTTGGTA 3050
TTGCCACCTC CATGGGTTTG GGTGTGCTTC AAATCAATGC CGGTCTGGAG 3100
CATTTATTTG GCTGGCCACA GGAAACCTGG CTGCAAATTG TCCTGATTGT 3150
GGTGGTTACC TCACTGGCTA CCTTATCTGT TGTCAGTGGA CTGGATGTTG 3200
GCATTCGCCG CCTGTCCGAA CTGAATTTGC TGGTTGCCAT TGCCCTTGATG 3250
CTGTTTGTGC TCGCCGTGGG CCC                               3273
```

FIG. 9c

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 5105
        ( B ) TYPE: nucleic acid
        ( C ) STRANDEDNESS: double strand
        ( D ) TOPOLOGY: linear ( x i ) SEQUENCE DESCRIPTION: SEQ ID NO:1:

```
CTGCAGGTAC  GAACCCCCTT  GCAGGAGCAA  GACGTGATAA  TCCGATGGAA        50
CAGCCAGGAC  ACGACGCACA  GCGGCGTCGG  TACGATGGGC  AAAATCCATG       100
AAAGGCTGGG  AACGATGGCT  GATTTCCATC  ACGGACACCC  CTGTGCCCGC       150
AAAATCAAGC  AGCTCATCAC  GTATTTGCAA  TAGAACATCC  ATTGGCAAGG       200
CGCTGGGCCC  TGCGCTGAAA  TTAAAGGGTC  GGGACATACT  TGCTGAGATC       250
CTGTACAAAC  CTGAACGCCG  GAACAGGCCC  CCCTATTTCG  GCAATGACAA       300
TCAAGTCTAC  GAGCACAATG  GTCTGATTAG  TCAGACCATT  AATATTCTCT       350
GGAGCAGACC  GCATGACGCG  TTCGTTTGAA  CTGGACACCT  TGAAGATGCG       400
TCTTAACGAT  GACGAACTTC  AATCCCTGGA  TCTTCACCAG  CGCATTCAGC       450
GTGCCTTGCG  GGCATTGATT  CTGGATGGCG  CCCTGGGTCC  CGGGGTCAAG       500
CTGCCTGCCA  CACGCTCCCT  GGCCAAATCT  CTGAGCATGG  CCCGCGATAC       550
GGTTGAAAAC  GCCTATGTTC  AGCTGCATCG  CGACGGCTTT  ATCGTGCGAC       600
GTGAAGGCTC  AGGCAGCTAT  GTTTCTGAAT  CGGTCGGCAC  GGAGCTGCGC       650
GGCAGTGCCT  ACCGTCGCAT  CAAAGCCCAG  GATCTGAAAC  GCAGCGTGAT       700
GGAACCCGGC  ACGGGTTTAA  GCCGCCGGGG  TCGCGCCGTG  TTTGAAAGTG       750
GCGGCATTGC  CGATCAACAG  ACCATCAAGG  CCTTTGCCAC  GGGTTTGCCA       800
GAAACCCGCA  ACTTCCCCAC  CGATGTGTGG  GAGCGCCTGC  AACGTCAGGC       850
CATGAAAGAC  TACCGGGCCA  ACATCCTGCT  GCATGGCGAC  CCGCAAGGCA       900
CCGAGTCCCT  GCGTAAAGCG  ATTGCCGTGT  ACCTGAATCT  GGAGCGTGGT       950
GCGAAAGTCT  CTGCCGATCA  AATTTTGATT  CTGAGCAGCA  CGCGCCAAGC      1000
CCTGTTCCTG  TGTGCGCAAT  TGCTGGTCGA  TGCTGGCAAA  CCCATTCTGG      1050
TCGAGAACCC  CGGCTACTTC  GGCGCCCGCA  AAGCCTTTGA  AGCGGCCGAG      1100
GCCCGTGTGG  TACCGATTGG  TGTAGACGAA  CAAGGTTTGC  GCACCGATTT      1150
GCTCAATGAA  GATCGCAGCG  GCGCAAACTG  TATTTATGTA  ACGCCCTCGC      1200
ACCAGTATCC  CACCGGGGCT  ACCATGTCCC  TGGAGCGTCG  TCTGGAACTC      1250
ATACACTGGG  CAGCAGAAAA  TGGCCGCTGG  ATTATGGAAG  ACGACTACGA      1300
```

| | | | | |
|---|---|---|---|---|
| CAGCGAATTT | CATTACGACG | GGCTACCCAC | GGCATGTGTG | CAAGGTCTGG | 1350
| ATAAATACCA | GCGCACCATC | TACCTGGGCA | CCTTCAGCAA | AACCCTGTAT | 1400
| CCGGGCCTGC | GCATGGGCTA | TATGGCCTTG | CCGCCCGAGC | TGGTCAAACC | 1450
| CTTTACCCAA | GCCCGCAGCA | TCATGGATGG | CCATACACCG | CAAATCCTGC | 1500
| AACTGACGCT | GGCGCGCTTT | ATGGAAGACG | GGCATTACAA | CTCTCATATT | 1550
| CGCGCCATGC | GCAAACTGTA | TGCCGGGCGA | CGAGAAATCA | TGCTGGAAGC | 1600
| CATCGAGCAG | CACTTGCAAG | GCATAGTCCG | TGCAGCTCGA | CCTGAAGGTG | 1650
| GTTTGCAGAT | TCCCTGCTTT | CTGGAGCCGG | GCTGGTCAGA | AGAACACACG | 1700
| CTGCGCCGCG | CTTTGAGTGC | GGGCGTTCAA | CTGCCAGGTT | TGAGCCGTCT | 1750
| GTACATTGGT | GAGGAAAAAC | AACAGGGCTG | GTTGCTGGGC | TATGCATCCC | 1800
| TGACCGCCTA | CGAGATCGAA | TCCGCCATGT | TGCGTCTGGC | CAACGCACTC | 1850
| CGCCAGGGCA | AAGGCTAGGT | CAGGAAAAAT | CAGTACATCA | AGGGGAATCG | 1900
| CCGGTTCAAG | TCGGCAACCC | CTTCCAGAAT | GGCATTCTCG | GTGCGGGGAT | 1950
| TGCGCGAACC | ACTGCGCACC | CCGCCCAGCA | AGGCCAGAAT | CATGTCGCCG | 2000
| ATTTCCTTGA | AATCGTCCTC | GCCCAAACCG | CGCGTGGTAC | AGGCGGCGCT | 2050
| GCCCACACGC | ACCCCGAGT | ACGCACCAGT | GACCTGCTCA | TAAGGCACCC | 2100
| GGTGCTTGCT | CAAGCTAATG | CCTAACTGAG | CCAGAACCCG | CTCCACCAAA | 2150
| GGCCCGGACA | AGTCCCAAGG | GCGCAAATCC | ACCACACCAA | AATGACAGTC | 2200
| TGTACCGCCT | GATACCACTG | TCAGCCCACC | TTCGGCCAAA | CGACGACACA | 2250
| AGCTGCGCGC | ATTGATGATG | ACGGACTGGG | CATAGGCCTT | ATAGGACGGA | 2300
| CTCATCGCCT | CACCCAAGGC | CACGGCCTTG | GCCGCCAGAA | TGTTCAGCAA | 2350
| AGGCCCGCCT | TGCAGCCCTG | GATACACCGC | CTGGCTCAAG | CGCTCGGCCA | 2400
| GCTTGGGTTC | ATTGCTCAGG | ATGATCCCGC | CACGCGGACC | GCGCAAGGTG | 2450
| CCATGCGTGG | AGAAAGTCGT | AACGTGCGCA | TGCTTGACGG | GCGACTCCAT | 2500
| CAGCCCCGCA | GCAACCAGTC | CCGCACTGTG | CGCCAAATCC | ACCATCAGGT | 2550
| AGGCATTGAC | CTCGTTGGCG | ATATTTCTGA | ACTCGGCAAA | ATTCGGGGTC | 2600
| CGTGAATAAG | ACGATCCTCC | GGCAATGATC | AGCCGTGGTC | GTTCCTTGTG | 2650
| AGCCAGAGCG | CGGACTTCAT | CCATGTCCAC | CCATTGCGTC | TGACGATCCA | 2700
| CCCCATACGA | GCAGGTCTGA | AACCAGCGTC | CGGACACATT | GAAATGCGAG | 2750
| CCATGGCTAA | GGTGCCCACC | CGCACTTTGG | TCCAGCGCCA | GAATCGTGTC | 2800
| GCCCGGTGAG | AGCAAGGCCA | GATACACCGC | CAGATTAGCC | TGACTGCCCG | 2850
| AGTGCGCCTG | CACATTGGCA | TAGGAGGCCC | CAAAAACCGC | CTTGGCCCGC | 2900
| TCGATGGCCA | GCTCTTCAGT | TTGATCGGCT | TGTTCGCACC | CGCCGTAAAT | 2950
| CCGTTGCCCA | GGATAGCCTT | GCGCCTGCTT | GTTGCTGAGC | AAGGAGCCCT | 3000
| GCACGTCCAG | AACGGAGCGG | CTCAGGTAAT | TCTCGGAAGC | GATCAGCTCA | 3050
| ATGGTGTGTT | GTTGGCGACG | CCGTTCGGCT | TCGATGATGT | CCCAAAGATT | 3100
| GCGATCGCTT | TGCTGTAGAA | ATTGCGAACC | CACCAGAGGC | AGGTGGGGGG | 3150
| TGTCGCCACC | GGCAAGACTC | TTCATGGGAG | TTCCTGTTTA | GAAATTGGCT | 3200
| ACTGTTGCCA | CCGTGCAGAC | TTTTCAAACA | CAGGCAAAAG | TGCAGCCCTG | 3250
| GCATGACGAT | TCCAAGGGCG | AAAGATAAAC | ATCCTATTCT | GTTTATCGAC | 3300
| CTATCAAACA | GTCCATTAAA | AATAAATCCA | CCAGACCACT | TTTAATTATT | 3350

```
GTTATTTGAA TAAACATTCA AAGCATAAAG AATTAAAAAT CACCTGAAAC        3400
CAAGCTATAA AGCCAATCCC GATTATTCTT GTCAACAATT AAAACAAGAT        3450
TCAAATTTTT ATTATTAAGT GGTCTGTTAA ATAGCCGAAA AATGGTCTGT        3500
CATTTATTGT CATAGGATCA TTAGAATGCA GCCAACGAAT ACTCAAGACC        3550
CATACTTCTA AACGCTCAAG CAGATTATCA CCTTTCTCTA TCTGCGCACG        3600
ATAAAAACAT CCTCAGTTTT CCCACGACTA CAGGAAACTC CATTGCTTTA        3650
ACGGCAGTTC AACCACGCTG ATCCCACGG TTTGAGAAAC CCGGCAACGG         3700
GATTTTTTG GGCCTTGTCC ATAAGAATCG GCAAATCCTT TTAAGCCTGC         3750
GAATTTCCAT TTGGAAATAA AGATGGGTGG AATAAGAAA CGACCTGTTC         3800
ATTTCGAACA GATCGCAATC AACAGCAAGG AAGTTTGAAA TGACAATCAA        3850
AAGCTACGAA ACTGATGACG CCGTACGTAA TATGCTGCAA AAGCTGTCTG        3900
TACTTTGGAA AAACCGGGCT GCCGTGAATC AGGAGCTGCC GGACTACAAC        3950
AATCTGGCGT TCGATCCCAA CAAGGCTGAC TTCAGCGAAT GCCTCTTGCC        4000
GTTCCGCGAG CATCAGGCCT GGCTGGAAGC ACCTGAAGAA TTGAAATCGC        4050
AGTGCTTGTC CTACGCTTGG GGCATTTACA ACCTCAAGAC CATTTATGTT        4100
GAATGCAACG TGGTCACCCC TTCTTGCGAA GACATCATCA AGACCCCGCC        4150
CCCAAGCGCC AACCGCAATC TGCTGCAAGA TGTGATGTCC CAGGCTTTGC        4200
TGGACGAGGC CCTGCACACG CGCATGTCGA TCATGGCCTG CAACTACATC        4250
TACTCCATGC GTGGTTTGAC GCCCCTGGAT TTCACCAATT CAACCTGGT         4300
GCAGTGGCGC AATGACATCC TGAGCCAGTG CAGCTCCGAA TCCGAGCGTC        4350
GCCTGACCCG CTTTGCCATT GCCTGCGCCT CCGAGACCCT GATTACCGAC        4400
TATCTGAAGA CCATGGCCGA GGACAAGAGC ATCCAGACCG TGTGCCATGA        4450
AGTCACCCGC ACTCACGCCA TGGACGAGTG GAGCCATTCC AGCGTGTTCA        4500
GCTTTGTGGC CTCCGACATC ATTCACGGCC TGAGCCAGAA AGAGCGCGAG        4550
CACATGCGTG CCGTGATTTT GCGCACCGTG GAAATGTTCG CCAACAATGA        4600
AATGGGTGCC TGGGAAAAGG TCTTCTCCAT GGTGAACTTC CCCAACGCTC        4650
GCGACATCTT GCACGACACC GGCGACTCCA ACGAAATTGG TGTGTACACC        4700
GGCTCGGTAG AAAGCCTGAT CGAGCGCATT GGCTTGAACA GCAAATCCGG        4750
CAAGGCCCAG CCCGAGGCCG AACAGCAGGA GGCGCTGCAA TGACAGCCAT        4800
GATTCAGGCG CGCTGCGAGA CCGTTCGCCC CGAGGCCGGG AACGTCAAAG        4850
TGTTTACCTT GCGAGTGCAA AGTGGCCACT TTGATTTTCT GAGCGCCTTG        4900
CGGGCAGGCA AGCATGTCGC CCTGAGCTAC CCCGATACCG GCGGCACCAT        4950
TCAACAGCGT ATGTATTCGA TCACCCGTGT GGCCGATCCA GACCTGATTG        5000
AAATTGCCGT GAAAGGGTCG GGCCGCAATA GCGTCTCCGA TCATCTGCAT        5050
GCCACCTTGC GCGAGGGCAT GAGTGTGCCC CTGCAATATG TGGCGGGTGA        5100
GATCC                                                        5105
```

( 2 ) INFORMATION FOR SEQ ID NO: 2:

( i ) SEQUENCE CHARACTERISTICS:
        ( A ) LENGTH: 3273
        ( B ) TYPE: nucleic acid
        ( C ) STRANDEDNESS: double strand
        ( D ) TOPOLOGY: linear ( x i ) SEQUENCE DESCRIPTION: SEQ ID NO:2:

```
GGATCTCGGT GGACTCGATT GTGGGTTACC AGCGTATCGC CATGATCGCC        50
GGCGGCATTG GCATTACCCT GCCCATTGCC TTGCTGCGTG AATTGGCGGC       100
GCGAGCCCAG GACGGCTTGC CTGTACCACA AGTACATTTG CTGCTCAGTA       150
TTGCCCGTAT TGCCGACATT CCTTTCCTGC ACGAGCTGCT GCAGCTGGAC       200
CTGGGCACCA GCTGGTTCAC ACTGACGGTG TTTGTCACGC AGGAAAAAAT       250
CCGCGAAAGC GCTCATTTCA AAGTGGGACG CCCCTCTTTT GAGAATATGG       300
AGCAATTGAA AGACCCGCAG GCCGTGGTGA TTTGCGGCAG CCATGGGTTT       350
GCCCAGGCCT TGCGCGAATA CACCATTCAG GCGCACCCCA TCTCGCACAT       400
GTTGATTGAA GCCTTCTCCC CACCGGCCAA AGCGGGTGTG GAAATCCTGC       450
CTGAAGCAGG CAGTGCCCCC TTGCAAATCA ATGTACGCAG CACCGGACAA       500
ACGCTCAACC CTGAGCCGGG CAGCAGCCTG CTGGAAATGC TGGAAGCAGG       550
CGATGTGCCT ATTCGCAGCC AATGCCGTTC GGGCATTTGC GGCGCTTGCC       600
GGGTACAGAT ATCGGAGGGC GAATACCGCT CCGAACCGGA CTTTTGCCTG       650
AGTGATCAGG ACAAGGCCCA GGGCCATGCG CTGGCGTGTT GCACCTTCCC       700
CCTGTCGGGT GCCATTAATG TAGACATCGG TACCACGAGC TGACATCCTT       750
ACCATCTGGA TTGAAAGAAA CTCTTATGAA GAAAGTCATC GCACTGCGTC       800
ATATCCATTT TGAAGACTTG GGCACACTGG AACCTGTTCT GATCGAACAG       850
GGCTACCAAG TTCAATATAT TGACCCTTCC GTCGAGTCAC TACGCCATGT       900
GGGTGAACAG GACGCTGACC TGCTGGTTGT ATTGGGCGGG CCAATCGGCG       950
CCTACGACGA AAAGATTTAC CCCTTCCTGT CCGATGAGCT GGAACTGATC      1000
AACAAGTTCT TGCTGGCAGG AAAACCCCTG CTGGGCATTT GCCTGGGCGC      1050
GCAACTGATT GCTCGTGCTC TGGGAGCCAA TGTGTATCCG CTGGGTGTGA      1100
AAGAAATCGG TTTCTCTCCC CTGAAACTGA GTGAAGCGGG CAAAGAATCG      1150
CCCCTGGCCG CCGTCAGCGG CATTCCCGTC CTGCACTGGC ACGGGGATCA      1200
GTTCGACATT CCCGATGGAG CCATTCACCT GGCCAGCACG GACGTAGGCC      1250
CCAACCAGGC CTTCTCCTTT GGAAGCCAGG TATTGGGTCT GCAATTTCAC      1300
CTGGAGGCCG ACACCAGCAA GCTGGAACGC TGGCTGGTTG GTCATGCCAA      1350
CGAACTGGGA CAAGCGGATA TCGACCCGCA GATGCTGCGT CTGGAAGCCA      1400
TGGCGGTACA AAAACGCCTG CACGCCGCTG CTGCTACGGT CCTGACCAAC      1450
TGGCTCAGCC AACTTAAACA AGCCAGTTCC GCTGATTGTG CTGCATGAAC      1500
ACTGCTGTAA CGTTTGTTGA TCGCRAACGA CATCCCTACC ATGTGGATGT      1550
CGTTTCGATT CAGTCTCAAG TGGTCTACGG TCGGGTGGGC AACAATGTTG      1600
CCGGCCCGAC CTTACGTAGG CACGGCTTTA AAGTCGCCGC CGTTCCCACC      1650
GTGTTGCTCA GCAACAACCC GCAATACCCC ACCGTGCACG GCGGTGCCGT      1700
CCCCGATGAA TGGCTGAAAG CTTTCTGGA TGACCTGGTG CTGCGTGGTG      1750
CGCTGGACAA GGTGCGCGCT GTCCTGATCG GTTATCTGGG CAGCGCCAAT      1800
CAGGCCGTCA TCATTGCGAA CTGGCTGAAG GCCTTGTTGC AAGACCATCC      1850
GGACACTCTG GTCATCGTGG ACCCGGTCAT AGGCGATCTG GATGTAGGAG      1900
TCTACGTAGA CCCGGCGCTG ATTCCCGCCT ATCACGAAAC CTTGCTGCCG      1950
CTGGCCACGG GCCTGACTCC CAATAACTAC GAGCTGTCCT TGCTGTCCCA      2000
```

```
ACAGCCTTGC GACACCATCC AGGGCAGTTC AAGCGCCGCG CACGCCTTGC         2050

TAAATGGCCG TACCGAATGG GTCATTGCTA CCAGCGCCGC TCCCGACTCC         2100

TGGCAGGATG GCCAGATCAA ATTATTAATG TCGCGCAAAG AACCCCGCGC         2150

CGACACCCTG CTTAGCCATC CTCGCGTCGA TTGTGCCGCC AAAGGCACCG         2200

GCGACCTGTT TGCCTCCACC TTGCTGGCCC ACCTGATTTT GGGTGCAGAC         2250

CTGCATTCGG CGGTGCATAC AGCCAGTGCC AGTGTGCTGC TTCAATTGGA         2300

GTTGACCCGA CAGGCCGGAC ATCAGGAATT AATTTTGCCG ATAGATCCTT         2350

TCCGAGCCTG AGCAAATATT TCTTAATCTA ACAAACCTTT CAACAGGCAG         2400

TCGTTCTCGT TAAGCTGTGC CCTCTTAGTT ACAAACGGAG CATGACATGG         2450

GGCTGCCTTT TAAAAGCACG CTACATCCAC GGGTGTTCTG GGGATCTACC         2500

TTTATCGTCC TGGTCTTTTT GCTGATCGGG ATTATTTCC CTAAAGACGC          2550

CGCACTTATT TTTGAGCAGT TACAAAACTG GGTCATCAAA AGTTTCGGCT         2600

GGTTCTATAT CCTGGCTGTG GCCTTGTTTT TCTTTGCCGT CGTCTATCTG         2650

GCATTAAGCC GCTACGGCAA CTTGAAATTA GGGCCGGACG ACTCGGAACC         2700

TGACTACCCG TATCTCACCT GGATGGCAAT GCTATTTGCC GCCGGTATGG         2750

GTATTGGTTT GATGTTCTTT GCCGTGGCCG AACCACTGCA ACACTTCTCG         2800

GCCCACCCT CGGGTCTGGC CAGCACAGTG GAAGCCGCCC ATCAGGCGCA          2850

GATCATCACC TTCTTTCACT GGGGCGTTCA TGCCTGGGCC GTCTATGCGG         2900

TCGTGGGTTT GTCGCTGGCC TATTTCTGCT TTCGCTACAA CCTGCCGTTA         2950

ACGATTCGCT CGGGCCTGTA TCCCTTATTT GGCAAGCGCA TTGAAGGCTG         3000

GATTGGCGAT AGCGTGGATA TTTTCGCCGT TTGCGGCACG CTATTTGGTA         3050

TTGCCACCTC CATGGGTTTG GGTGTGCTTC AAATCAATGC CGGTCTGGAG         3100

CATTTATTTG GCTGGCCACA GGAAACCTGG CTGCAAATTG TCCTGATTGT         3150

GGTGGTTACC TCACTGGCTA CCTTATCTGT TGTCAGTGGA CTGGATGTTG         3200

GCATTCGCCG CCTGTCCGAA CTGAATTTGC TGGTTGCCAT TGCCTTGATG         3250

CTGTTTGTGC TCGCCGTGGG CCC                                      3273
```

BACTERIAL STRAINS FOR BIOREMEDIATION

CROSS-REFERENCES TO RELATED APPLICATIONS

This application is a continuation-in-part of our prior application Ser. No. 08/049,281, filed Apr. 13, 1993, now abandoned.

FIELD OF THE INVENTION

This invention relates to genetically modified microorganisms which have improved capabilities for bioremediation of ammonia and other chemicals such as halogenated hydrocarbons, amines, phenol and benzene. More particularly, this invention relates to genetically manipulated microbial strains which have superior capabilities for degrading ammonia and other chemicals, such as halogenated hydrocarbons, amines and benzene, compared to their natural counterparts.

PRIOR ART

Ammonia is a common industrial waste product and a common agricultural fertilizer. The discharge of ammonia from industrial and agricultural sources is a serious environmental problem. It is therefore imperative to devise technologies which effectively remove ammonia from industrial and agricultural waste streams. This particular problem lends itself well to bioremediation. There are a number of naturally occurring microorganisms which can oxidize ammonia to nitrite or nitrate.

The metabolic process of converting ammonia to nitrite by microorganisms is known in the art as nitrification, which involves two enzymes: ammonia monooxygenase (AMO) and hydroxylamine oxidoreductase (HAO) (Hooper, A. in *Autotrophic Bacteria* Biochemistry of the Nitrifying Lithoautotrophic Bacteria; Schlegel and Bowien, Eds,; Science Tech Publishers: Madison, Wis. 1989; Chapter 13, pp 239-265). AMO catalyzes the conversion of ammonia to hydroxylamine, and HAO catalyzes the oxidation of hydroxylamine to nitrite.

AMO appears to be a metalloenzyme and is closely associated with the cytoplasmic membrane. Because AMO has not been isolated, its structure and molecular weight are not well characterized. AMO is a nonspecific enzyme which is able to oxygenate a wide range of substrates including ammonia, benzene, ethylene, phenol, propane, amines and halogenated hydrocarbons.

HAO has been characterized by both chemical and biochemical techniques (Hooper, A. in *Autotrophic Bacteria* Biochemistry of the Nitrifying Lithoautotrophic Bacteria; Schlegel and Bowien, Eds,; Science Tech Publishers: Madison, Wis. 1989; Chapter 13, pp 239-265). It has an $M_r$ of approximately 180,000 daltons and is a highly complex hemoprotein. HAO consists of 3 $\alpha$ subunits ($M_r$ 63,000) and 3 $\beta$ subunits ($M_r$ 11,000). The enzyme is fully active without the $\beta$ subunit but less stable.

However, very few molecular-biological analyses have been performed to investigate the genes encoding the AMO and HAO enzymes and their regulation. The only available reference is by Tokuyama et al. (Japan, *Hakko Kogaku Fermentation Engineering*, 1988 66, 103-107). They describe the cloning of the hao gene from a bacterium, *Nitrosomonas europaea*. *N. europaea* is a nitrite bacterium, which acquires energy from oxidizing ammonia into nitrous acid and is known to be inhibited in the presence of organic carbon matters. Such inhibition occurs when other heterotrophic organisms that can better utilize organic carbon matters inhibit the growth of *N. europaea* by outgrowing it or when certain organic carbon matters directly interfere with the activity of the AMO enzyme by occupying the active sites of the enzyme. A chromosomal DNA from *N. europaea* was completely digested with the restriction enzyme EcoRI and cloned into *Pseudomonas putida*. Over 3000 individual colonies were screened for hydroxylamine utilization using a color assay (Rider et al. *Indo Eng. Chem. Anal. Ed.* 1946, 18, 96-99). One clone which expressed HAO activity was isolated and characterized. This plasmid contained a 4.7 kb insert of Nitrosomonas DNA. HAO enzyme assays showed that the expressed heterologous gene in P. putida had approximately 10% of the activity level of the enzyme in its native donor strain, and subcloning experiments showed that of the 4.7 kb of DNA originally cloned, a minimum of 3.7 kb is required for any appreciable activity.

In addition to Nitrosomonas, which is viewed as an efficient ammonia oxidizer, there are other well known nitrifying microorganisms that utilize carbon compounds as well as ammonia as energy sources, which include the bacterial genera Arthrobacter and Alcaligenes, and the fungi genera Aspergillus, Penicillium, and Absidia.

In commercial bioremediation systems, Nitrosomonas strains are generally employed to remediate ammonia. As stated above, Nitrosomonas strains are inhibited in the presence of organic carbon. Consequently, it is customary to remove organic materials in as many as three bioreactors before the remaining waste is treated in a nitrification reactor containing Nitrosomonas (Dombrowski et al., *Bio Engineering*, 1989, 5, 18-21).

It would be desirable to provide genetically modified microorganisms that are not only unaffected by but also able to metabolize organic carbons and are highly efficient nitrifiers such that the modified heterotrophic microorganisms can be utilized in the remediation of various waste-matters.

SUMMARY OF INVENTION

There is provided in accordance with the present invention a recombinant plasmid adapted for transformation of a host microorganism, the plasmid comprising a plasmid vector into which a polydeoxyribonucleotide segment that codes for ammonia monooxygenase and hydroxylamine oxidoreductase has been inserted, the polydeoxyribonucleotide segment derived from a donor selected from the group consisting of *Nitrosomonas europaea, Alcaligenes faecalis, Alcaligenes eutropus, Pseudomonas aeruginosa, Arthrobacter sp., Arthrobacter simplex* and *Absidia cylindrospora*, wherein the resulting transformant exhibits at least 50% of the overall level of ammonia monooxygenase and hydroxylamine oxidoreductase activity of the donor.

In accordance with the present invention, there is also provided an isolated polydeoxyribonucleotide segment comprising codons for ammonia monooxygenase and hydroxylamine oxidoreductase, the polydeoxyribonucleotide segment derived from a donor selected from the group consisting of *Nitrosomonas europaea, Alcaligenes faecalis, Alcaligenes eutropus, Pseudomonas aeruginosa, Arthrobacter sp., Arthrobacter simplex* and *Absidia cylindrospora*, wherein the segment is capable of transforming a host microorganism to nitrify ammonia.

There is further provided a transformant microorganism which contains at least one copy of a recombinant plasmid, the plasmid comprising a plasmid vector into which a polydeoxyribonucleotide segment which codes for ammonia monooxygenase and hydroxylamine oxidoreductase has been inserted, the polydeoxyribonucleotide segment derived from a donor selected from the group consisting of *Nitrosomonas europaea, Alcaligenes faecalis, Alcaligenes eutropus, Pseudomonas aeruginosa, Arthrobacter sp., Arthrobacter simplex* and *Absidia cylindrospora,* wherein the transformant exhibits at least 50% of the overall level of ammonia monooxygenase and hydroxylamine oxidoreductase activity of the donor.

Additionally, there is provided a process of remediating or oxidatively converting ammonia from wastestreams which comprises growing the transformant microorganism of the present invention. The present transformant microorganism can also be employed to oxidatively convert compounds selected from the group consisting of halogenated hydrocarbons, amines, aliphatic hydrocarbons, benzene, phenol, cyclohexane, methanol, sulfide, and ammonia by growing the transformant in a solution of the compounds.

BRIEF DESCRIPTION OF THE DRAWINGS

The invention will be more fully understood and further advantages will become apparent when reference is made to the following detailed description of the invention and the accompanying drawings in which:

FIGS. 5(a), 5(b), and 5(c) show the nucleotide sequence of the hao region.

FIGS. 9(a), 9(b), and 9(c) show the nucleotide sequence of the amo region.

DESCRIPTION OF THE INVENTION

Figure 1:
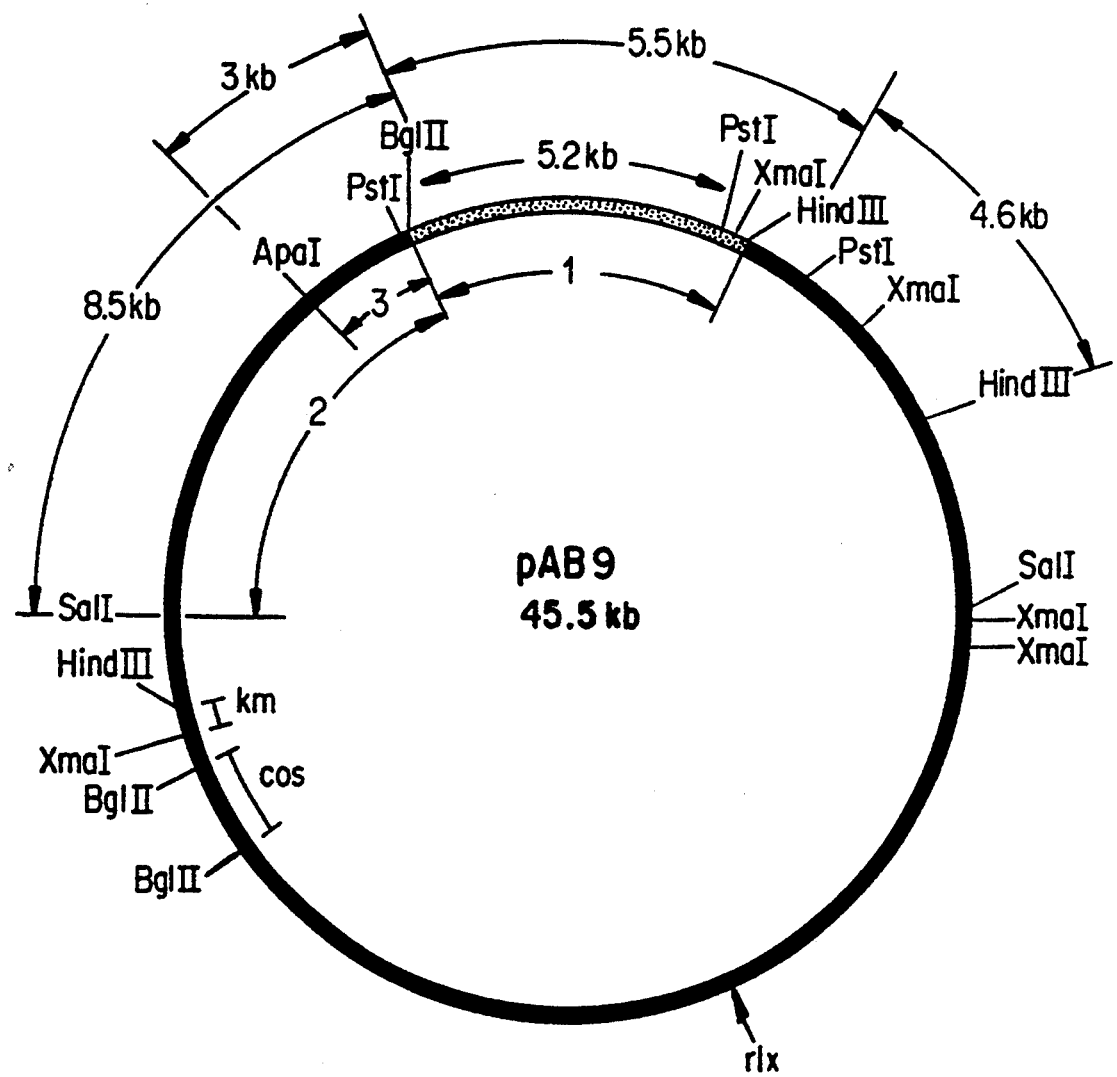
FIG. 1 is a restriction map of transformed plasmid pAB9.

The present invention provides modified microorganisms that are fast-growing heterotrophic nitrifiers. The present modified microorganisms contain a cloned DNA fragment comprising codons that code for the enzymes AMO and HAO. The microorganisms thus modified are suitable for the use in bioremediation of ammonia. In addition, the modified microorganisms are suitable for the use in oxidative-conversion of a variety of compounds including aromatic and aliphatic hydrocarbons as well as oxidizable inorganic chemicals, e.g., halogenated hydrocarbons, such as dichloroethane, trichloromethane, trichloroethylene, tetrachloroethylene, carbon tetrachloride, chloroform and the like; amines, such as methylamine, diethylamine, tri-n-propylamine, N-phenylhydroxylamine, puridine and the like; aliphatic hydrocarbons, such as ethane, propane, butane and the like; benzene; phenol; cyclohexane; methanol; sulfide and the like. Unlike the natural nitrifiers, the modified microorganisms efficiently consume or convert ammonia and other chemicals from the media that contain ammonia and/or other substrate chemicals as well as carbon and other organic compounds, and are fast growers that compete well with other natural microorganisms.

The methods suitable for the present modification process are well known in the art as disclosed, for example, by T. Maniatis et al., *Molecular Cloning,* Cold Spring Laboratory, 1982, and the typical process comprises, briefly: (1) isolating cytoplasmic DNA strands from a suitable donor, (2) digesting the DNA strands with restriction endonuclease enzymes, (3) isolating the digested DNA fragments, (4) ligating the isolated recombinant DNA fragments to a suitable transfer vector, (5) transforming a host organism with the recombinant DNA, and (6) detecting and selecting the functional transformants.

The suitable donors are selected from naturally occurring nitrifiers known in the art, which include nitrifying procaryotes and eucaryotes. Illustrative of the suitable donors are nitrifying gram-negative bacterial species such as Thiosphaera, Nitrosocystis, Nitrosomonas, Pseudomonas and Alcaligenes, gram-positive bacterial species such as Arthrobacter, and fungal species such as Aspergillus and Penicillium.

Of these, the preferred donors are efficient nitrifiers as defined by having a low apparent Michaelis-Menten constant, $K_m$, and a high apparent maximum velocity, $V_{max}$. The apparent $K_m$ and the apparent $V_{max}$ are well known in the art and the terms are well defined, for example, in *Principles of Biochemistry,* A. L. Lehninger, p 212–217, Worth Publishers, Inc., 1982. For example, the apparent $K_m$ values for *Nitrosomonas europaea, Alcaligenes faecalis* DSM30030 and *Arthrobacter sp.* are 7.5, 10 and 9 mg $NH_3$-N/liter, respectively, and the apparent $V_{max}$ values for *Alcaligenes faecalis* DSM 30030 and *Arthrobacter sp.* are 0.07 and 0.012 mg $NH_3$-N/mg protein/hour, respectively. The preferred donors also need to be easily grown and genetically manipulable microorganisms. The preferred donors include *Nitrosomonas europaea, Alcaligenes faecalis, Alcaligenes eutropus, Pseudomonas aeruginosa, Arthrobacter sp., Arthrobacter simplex* and *Absidia cylindrospora.* The more preferred include *Nitrosomonas europaea, Alcaligenes faecalis, Alcaligenes eutropus* DSM 428, *Pseudomonas aeruginosa* DSM 50071 and *Arthrobacter sp.* DSM 312. The most preferred is *Alcaligenes faecalis* for its high apparent $V_{max}$ value.

Although the present invention, for illustration purposes, discloses the gene sequence and restriction maps of the amo and hao genes of Alcaligenes, the analogous genes from other species of donors can be identified and isolated by well known processes in the art including hybridization processes. Such hybridization processes are disclosed, for example, in *Molecular Cloning,* supra, and *Current Protocols in Molecular Biology,* F. Ausubel et al., Greene Publishing Associates, 1989. Briefly, the hybridization process comprises (1) isolating the DNA fragments for the amo and hao genes from an Alcaligenes, (2) labeling the DNA fragment for use as a probe with a radioactive or fluorescent marker, (3) contacting a pool of denatured, restriction enzyme-digested chromosomal DNA fragments from a donor organism to the probe to hybridize, (4) washing off unhybridized DNA fragments, and (5) isolating and identifying the hybridized donor DNA fragments. Using such a gene identifying process in conjunction with the amo and hao genes of the present invention, the genes for AMO and HAO can be isolated from the above-identified donors.

The suitable host organisms suitable for the present invention preferably have good growth characteristics and an appropriate membrane structure, and do not utilize nitrous acid reduction metabolic pathways that remove nitrous compounds from their growing environment, i.e., do not reduce nitrite back to ammonia. A suitable host organism should be able to utilize diverse carbon energy sources and be a hardy organism that successfully competes with other natural microorganisms that are present in the waste-matters to be remediated. These requirements are important in that when the present modified microorganisms are employed in bioremediation of, for example, wastestreams, the modified microorganisms will have to utilize varying carbon energy sources that will be present in different wastestreams, and must compete with naturally occurring, competing microorganisms, which will inevitably be present in the wastestreams.

A suitable host preferably has a membrane structure similar to that of the selected donor. It is known in the art that the AMO enzyme is associated with the cytoplasmic membrane. Therefore, the AMO enzyme translated from the cloned gene may not be fully functional or even nonfunctional if the cytoplasmic membrane structures of the donor and the host are significantly different. Consequently, it is preferred that a gram-negative host be utilized for cloning of the genes derived from a gram-negative donor and a gram-positive host be utilized for the genes from a gram-positive donor.

In addition, a suitable host organism should not utilize nitrous reduction metabolic pathways that converts nitrite and nitrate, the end products of the nitrification reaction, back to ammonia, since such metabolic pathways reduce the nitrification efficiency of the modified organisms.

Illustrative of the suitable host microorganism for the present invention are microorganisms of the genera Pseudomonas, Paracoccus, Thiobacillus, Rhodopseudomonas, and the like, since they do not utilize nitrous reduction metabolic pathways. Of these, the preferred are Pseudomonas strains, which are common soil bacteria that grow at a relatively broad range of temperatures and under a variety of conditions. In addition, Pseudomonas are known to harbor a number of degradative pathways for toxic compounds, such as toluene, and chlorinated hydrocarbons. Such degradative pathways could be combined with the present nitrification modification to create efficient microorganisms that are capable of remediating a variety of toxic compounds. The more preferred are P. putida, P. aurofaciens, P. aeruginosa, P. stutzeri and the like. The most preferred is *Pseudomonas putida*.

Suitable transfer vectors for cloning the amo and hao gene segments of the present invention may vary with the host organism. Suitable vectors for different host organisms are well known in the art. Suitable vectors for different microorganisms are disclosed, for example, in *Cloning Vectors, A Laboratory Manual*, P. Pouwels et al., Elsevier, 1985. As an illustration, the suitable transfer vectors for Pseudomonas include cosmids, i.e., cos containing plasmid, such as pVK102, and plasmids, such as pSP329, pRK248, pRK252, pRK2501, pTJS75, pTJS26, pTJS130 and the like.

As is known in the art, it may also be advantageous to utilize an intermediary host, such as E. coli, that is highly suitable for and extensively utilized in conventional gene cloning/manipulation procedures, if the final host is an organism that is known to be not highly amenable to the gene cloning procedures. Such an intermediary host can be efficiently transformed with the DNA fragment of the amo and hao genes, and the intermediary host can then be induced to conjugate with the final host to transform the host to contain the amo and hao genes. For example, an E. coli transformed with the amo and hao genes can be induced to mate with a Pseudomonas, instead of directly cloning into Pseudomonas, which is not an efficiently transformable host with conventional direct cloning procedures.

Figure 2:
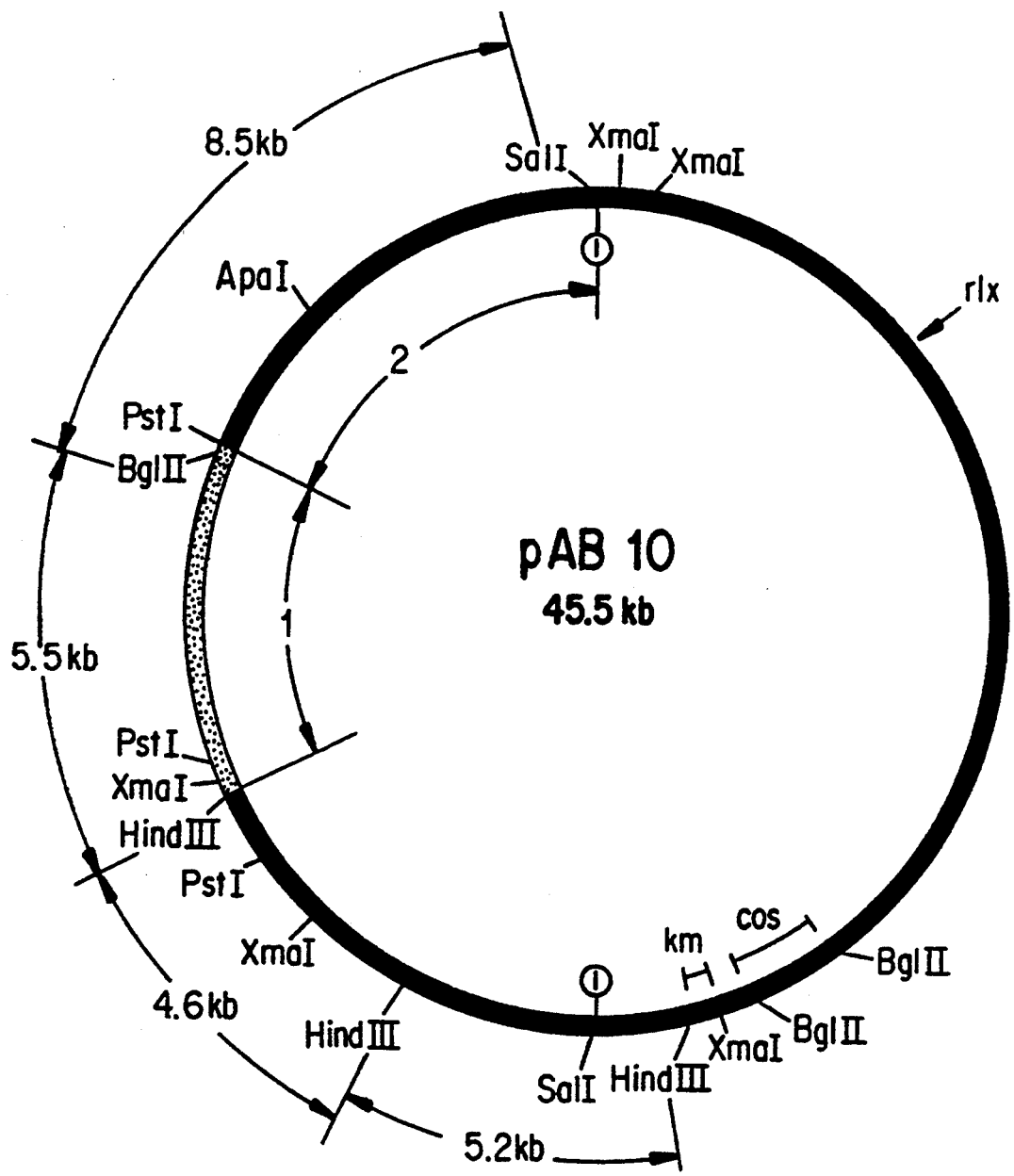
FIG. 2 is a restriction map of transformed plasmid pAB10.

The present invention can be better understood by directing to the figures for purposes of illustration. FIG. 1 represents one embodiment of the present invention (pAB9) and as exemplified in cosmid pVK102 with the inserted SalI DNA segment of about 23 kb that encodes the amo and hao genes, which was isolated from *Alcaligenes faecalis*. FIG. 2 represents another embodiment of the invention (pAB10), which contains the 23 kb SalI fragment in the reverse orientation to pAB9. The recombinant DNA segment can be transferred to any one of the above-listed suitable hosts to transform the host to be a highly efficient, fast-growing nitrifying microorganism. The nitrifying activities of pAB9 and pAB10 are clearly demonstrated in the examples, infra.

The transformant P. putida (pAB10), for example, exhibits several advantages over the host and donor organisms: the rate of disappearance of ammonia from the culture medium is approximately 3.5 times faster than for A. faecalis per unit cells; the growth rate of the recombinant organism is approximately 4.25 times faster than that of A. faecalis; the intermediate of the nitrification reaction, hydroxylamine, is converted to nitrite at a rate of about 6-fold higher than that of A. faecalis and P. putida; and ammonia is converted into nitrite at a 2.5-fold higher rate than for A. faecalis. Not only are these modified organisms of the present invention capable of removing ammonia at a faster rate, they also have significantly improved growth characteristics, making them efficient heterotrophic nitrifiers that are capable of growing at a fast rate under a variety of culture conditions. These results demonstrate the improved characteristics of the genetically engineered microorganisms of the present invention over their natural host. The transformant P. putida (pAB10) has been deposited in the permanent collection of the Northern Regional Laboratories, Agricultural Research Services, U.S. Dept. of Agriculture, Peoria, Ill., USA, under the accession number NRRL B-18893.

Although it is not wished to be bound by any theory, the improved characteristics of the present modified microorganisms over the donor and host may be explained by a gene dosage effect. It is theorized that multiple copies of the cosmid pVK102 are present in each transformed microorganism (pAB9 and pAB10), and the presence of the multiple plasmids increase the expression level of both enzymes in the modified microorganism and lead to the elevated efficiency. Additional genetic manipulations can be undertaken to further increase the efficiency of expression of the amo and hao genes. These enzyme-encoding genes can be attached to strong constitutive (lpp) or regulatable promoters to increase the level of expression even further. Examples of such promoters are promoters inducible by heat ($\lambda p_L$), by addition of a chemical (lac) or by deficiency of a nutrient (trp). The most preferred promoters are the E. coli lac and Sac promoters which are constitutive in Pseudomonas due to the absence of the lac repression gene and is inducible by isopropyl β-D thiogalactopyranoside in E. coli. The native promoter sequence or the coding sequence of the enzymes themselves can also be genetically altered to improve their efficiencies.

Figure 3:
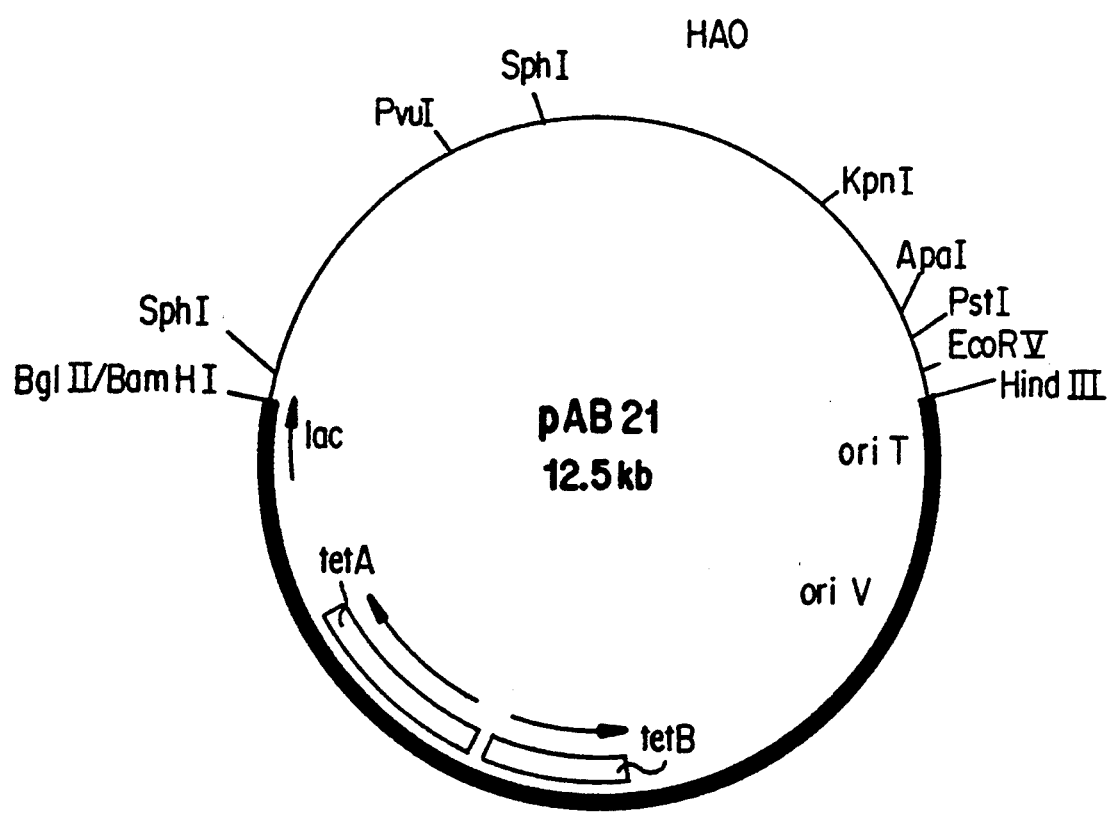
FIG. 3 is a restriction map of transformed plasmid pAB21.
Figure 4:
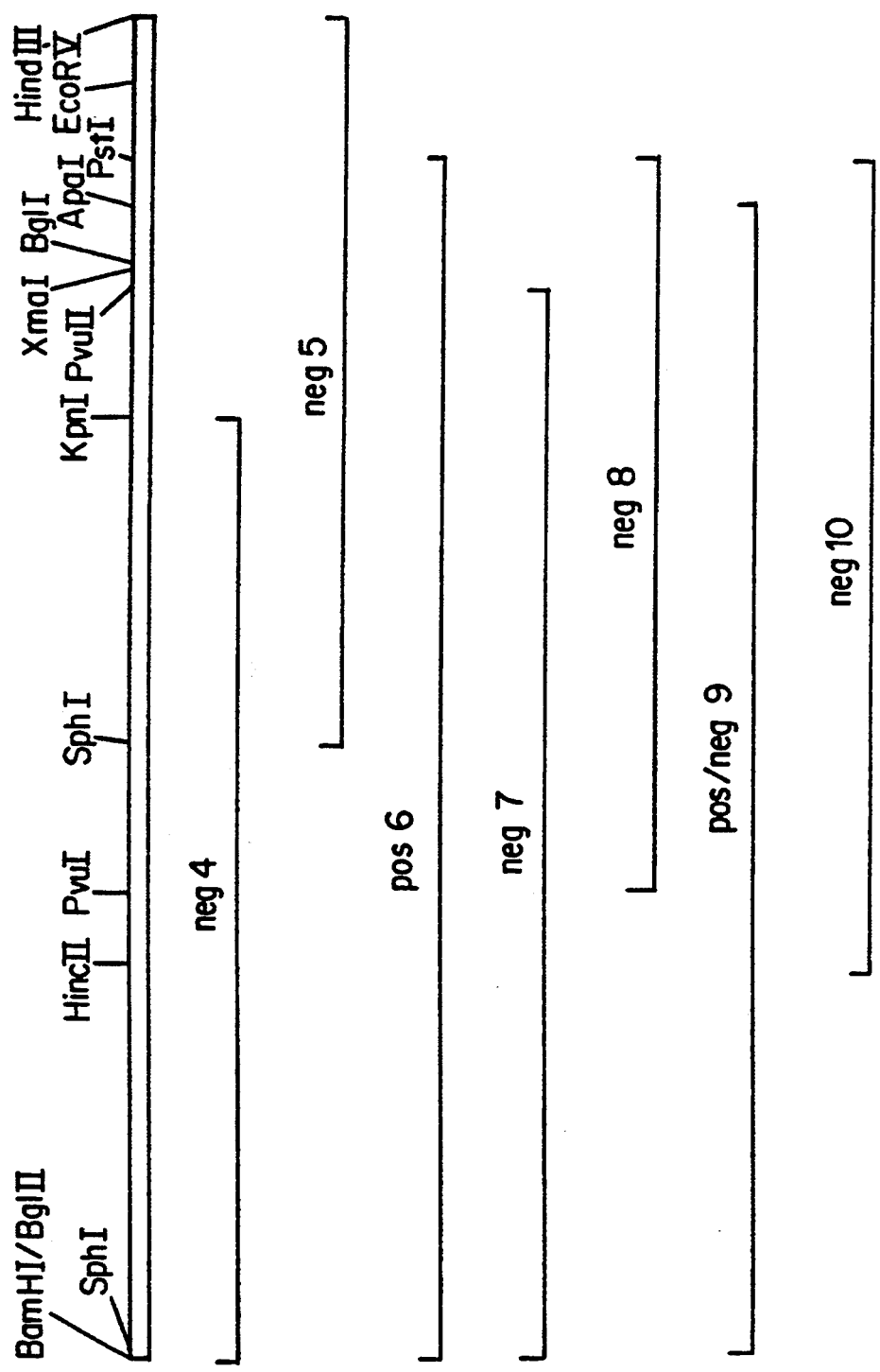
FIG. 4 is a restriction map of the region of pAB9 containing the hao gene.

FIG. 3 represents another embodiment of the invention (pAB21). The transformed vector pAB21 contains a DNA segment of about 5.5 kb of nucleotides that encodes the hao gene, which is a subsegment of the SalI segment between BglII and HindIII (1 in FIG. 1), ligated to plasmid pSP329. This subfragment has been demonstrated to contain the fully functional hao gene sequence. This 5.5 kb hao gene segment has been further subjected to subcloning experiments. The results are as shown in FIG. 4 and further discussed in Example IV, infra. The subcloning experiment results indicate that the DNA segment between the BglII and PstI restriction sites that consists of about 5.1 kb encodes the HAO enzyme. This hao gene has been sequenced as shown in FIG. 5 (SEQ ID No:1).

It is to be noted that the restriction sites identified as the hao gene sequence of the present invention do not correspond to those identified as the hao clone by above-mentioned Tokuyama et al. which was obtained from Nitrosomonas europaea. In spite of these differences, the genes are functionally analogous. Because of the degeneracy in the genetic code, i.e., more than one DNA sequence code for an amino acid, differences in the gene sequence of analogous proteins among different organisms often occur, although there are no or substantially no differences in amino acid sequences and in their activities. In addition, the substitution of one amino acid with another amino acid of similar size and charge does not necessarily alter the activity and properties of a protein, providing a homologous protein, as defined below. Such different nucleotide sequences, originating from different species, that encode practically an identical amino acid sequence or amino acid sequences containing limited sequence variabilities that exhibit the same functionality are known in the art as homologous sequences. It is generally considered in the art that genes which are functionally analogous may show up to about 30% diversity in their gene sequence; i.e., their DNA sequences are at least about 70% homologous. For example, *Applied and Environmental Microbiology*, G. Smith et al., Jan. 1992, Vol 58, No. 1, p 376–384, discloses that the dissimilatory nitrite reductase gene from P. stutzeri JM300 nir is 67% homologous to that of P. aeruginosa nir and 88% homologous to that of P. stuteri ZoBell nit. V. Desiraju et al. in *Journal of Bacteriology*, , Jan. 1993, Vol 175, No. 2, p 541–543, reported that the mutB gene of *Salmonella typhimurium* is 91% homologous to that encoded by the E. coli mutY gene. The homology of the present gene sequences preferably is at least about 75%, more preferably about 80%, and most preferably about 90%, in order to ensure the homologous gene sequences translate into fully functional HAO and AMO.

Figure 6:
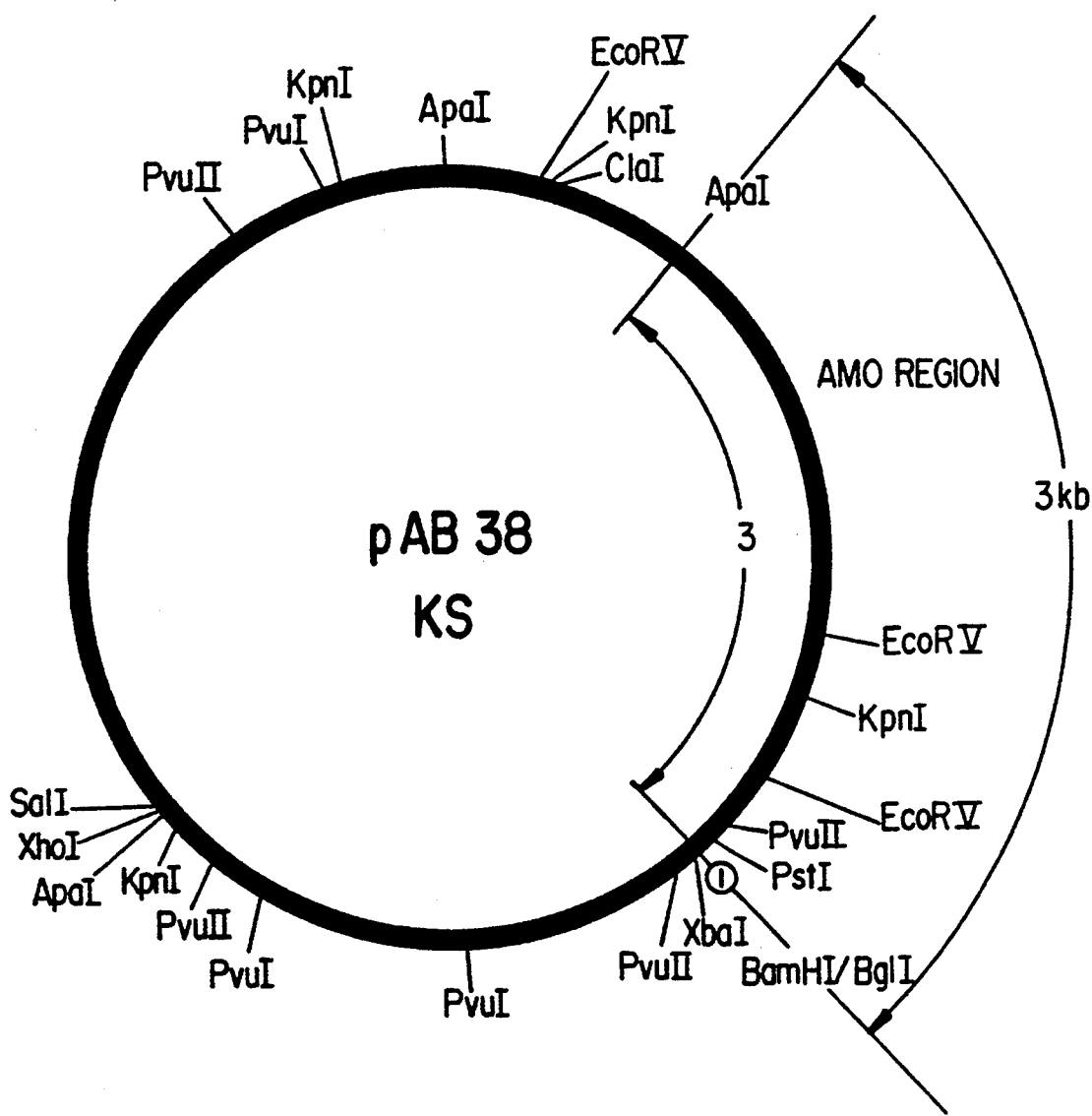
FIG. 6 is a restriction map of transformed plasmid pAB38.

FIG. 6 represents yet another embodiment of the present invention (pAB38). The plasmid pAB38 contains a subsegment between the SalI and BglII restriction sites (2 of FIG. 1), which consists of about 8.5 kb, of the 23kb SalI segment containing the amo and hao genes. The host organisms transformed with pAB38 exhibit enzymatic activities of the AMO enzyme. Further subcloning experiments revealed that the DNA segment between ApaI and BglII 3 of about 3 kb contains the minimum gene sequence that is necessary to express the AMO activity. This amo gene has been sequenced as shown in FIG. 9 (SEQ ID No:2).

Figure 7:
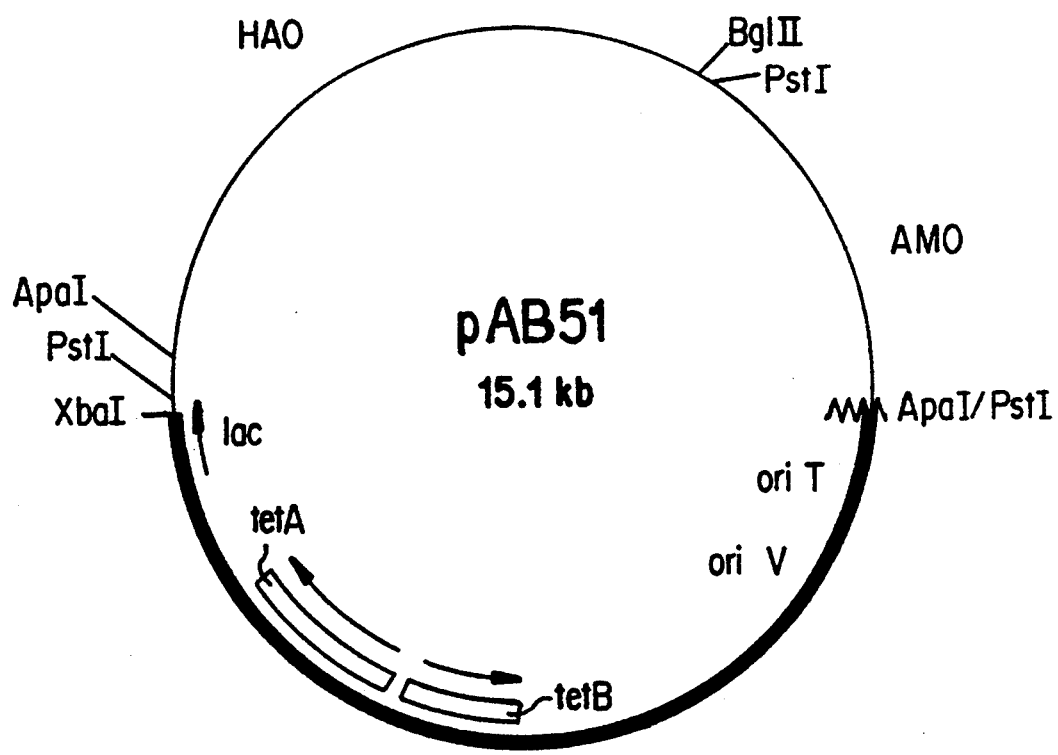
FIG. 7 is a restriction map of transformed plasmid pAB51.

FIG. 7 (pAB51) represents yet another embodiment of the invention that contains a DNA segment of about 8.1 kb, which is a subsegment between ApaI and PstI of the SalI amo and hao segment, that encodes the essential gene segments for the amo and bag genes. The plasmid pAB51 was constructed based on the discoveries that fully functional HAO can be produced from the above-mentioned 5.1 kb gene segment between BglII and PstI and that removing the 5.5 kb segment between SalI and ApaI does not inhibit the AMO activity, as further discussed in Example IX, infra. Therefore, the BglII restriction site serves as the junction point between the hao-containing fragment (PstI-BglII) and the amo-containing fragment (BglII-ApaI). In addition, as demonstrated in Example X, pAB49, the gene cloning procedure utilized to produce pAB51 can be used to construct vector plasmids having more than one copy of the amo gene and the hao gene in order to differentially express the activity levels of one or both of the enzymes.

It is important to note that the hao clone described by the above-disclosed reference by Tokuyama et al. only demonstrates about 8% of the HAO activity of the native donor strain. The transformed microorganisms of the present invention preferably have at least about 50%, more preferably at least about 100%, and most preferably at least about 150%, of the HAO and/or the overall HAO and AMO activity levels of the donor organisms such that the transformed microorganisms are efficient enough to be useful in large-scale remediation or conversion applications. For example, the present clones P. putida (pAB9), P. putida (pAB10) and P. putida (pAB51) exhibit over 560%, 660% and 700% activity levels, respectively, of HAO over its native gene donor, which are significant improvements over the prior art. In addition, the overall efficiency of the AMO and HAO metabolic pathways of P. putida (pAB9), P.putida (pAB10) and P. putida (pAB51) has been demonstrated to be over 110%, 250% and 1400%, respectively, of the donor, A. faecalis. All of these values were obtained with equivalent concentrations of cells and do not take into account the superior growth characteristics of P. putida over A. faecalis.

The transformed heterologous microorganisms of the present invention are highly suitable for use in bioremediation or oxidative-conversion of ammonia and other chemicals, including aromatic and aliphatic hydrocarbons as well as oxidizable inorganic chemicals, such as halogenated hydrocarbons, amines, aliphatic hydrocarbons, benzene, phenol, cyclohexane, methanol sulfide and the like, since they are highly efficient nitrifiers and fast-growing microorganisms that are not sensitive to carbon energy sources and can compete well with other naturally occurring microorganisms. The transformed microorganisms of the present invention may be grown to remediate a variety of pollutants in any suitable bioreactors known in the art. The terms "grown" and "growing" as used herein indicate not only the actively multiplying growth phase in the life cycle of microorganisms but also indicate the metabolically active phase where no or minimal increase in the cell density occurs. In addition, the present invention represents the first reported case of cloning and heterologous expression of the amo gene, and also the first to express the amo gene in a heterologous host.

The following examples are presented to more particularly illustrate the invention and are not to be construed as limitations thereon.

EXAMPLES

Assay procedures used:

(A) Ammonia Assay

Samples were assayed for ammonia using reagents from Sigmas "Urea Nitrogen" kit (Catalog #640). In an 18 ml test tube, 100 μl of sample, 1 ml of phenol nitroprusside, 1 ml of alkaline hypochlorite and 5 ml water were combined, vortexed, and incubated for 20–30 min at room temperature. Blue color indicated the presence of ammonia. The absorbance of 1 ml of the sample was determined at $A_{570}$. Standards were created using concentrations of ammonia at 0, 10, 25, 50, 60, 75 and 100 ppm, prepared from a 100 ppm Ammonia as Nitrogen Standard (Orion). The standards were assayed as described above, and used to make a standard curve, from which unknown concentrations were determined.

(B) Nitrate Assay

Hachs procedure for assaying nitrate was followed. In an 18 ml test tube, 2.5 ml of sample were diluted with an equal volume of sterile water, the contents of a Hach Nitra Ver 5 Nitrate Reagent pillow were added, and the mixture was vortexed for 1 min. The samples were incubated at room temperature for 10 min. The absorbance of 1 ml samples was recorded at $A_{500}$. The following concentrations of nitrate were prepared from a 100 ppm Nitrate as Nitrogen Standard (Orion): 0, 5, 10, 15 and 20 ppm. These standards were assayed as described above. The values obtained were used to make a standard curve and determine the unknown concentrations of the samples.

(C) Nitrite Assay

Hachs procedure for determining nitrite is identical to the nitrate except that a Nitri Ver 3 Nitrite Reagent pillow is added to the sample. The samples turned a range of pink, representing the nitrite content. Before reading the absorbance, the samples were spun for 2 min in a microcentrifuge to pellet any remaining bacteria. The following nitrite standards were prepared: 0, 0.025, 0.05, 0.1, 0.15, 0.2, 0.5, 1.0, 1.5 and 2.0 ppm. These were taken from a fresh stock of 100 ppm nitrite standard, 493 mg/l $NaNO_2$.

(D) Protein Assay

Bio-Rads Microassay Procedure for determining protein was followed. Initially, the samples were sonicated for three-10 second intervals. Then, in an Eppendorf tube, 100 μl of the sample were combined with 700 μl of sterile water and 200 μl of Bio-Rads Dye Reagent Concentrate. The mixture was vortexed and incubated at room temperature for at least 5 min (not more than 1 h). The absorbance of 1 ml aliquots was determined at $A_{595}$. The following standards were prepared using a 0.5 mg/ml stock solution of Bio-Rads Protein Assay Standard I, Bovine Plasma Gamma Globulin Lyophilized: 0, 0.625, 1.25, 5.0, 7.5 and 10.0 μg/μl. From these values a standard curve was created and the unknown concentrations determined.

(E) Ammonia Utilization

The initial velocity of ammonia utilization was determined in units of mg $NH_3$-N/mg protein/hour. The values were plotted on a reciprocal plot as substrate concentration [S] (x-axis) versus [S]/velocity V (y-axis). The y intercept of the resulting straight line equals $K_m/V_{max}$ and the x intercept equals $-K_m$. From these two interception points, the apparent $K_m$ and the apparent $V_{max}$ can be calculated.

EXAMPLE I

Construction of the A. faecalis Library

A 400 μg sample of chromosomal *Alcaligenes faecalis* DNA, which was isolated from A. faecalis DSM 30030 and cesium-chloride purified in accordance with the procedure outlined in *Molecular Cloning*, T. Maniatis et al., Cold Spring Laboratory, 1982, was digested with SalI (4 U/μg) at 37° C. for 100 min, resulting in partially digested fragments of 15–28 kb in size. One hundred micrograms (100 μl) of the SalI-restricted Alcaligenes DNA were heated at 65° C. for 5 min, and then carefully loaded onto a linear sucrose gradient having a concentration gradient of from 10% to 40%. The samples were centrifuged in a Beckman ultracentrifuge at 25° C. and 25,000 rpm overnight.

Starting from the top of the gradient, 500 μl aliquots were removed for a total of 24 aliquots. Five microliters of Type III Loading Buffer, which was prepared in accordance with the above-referenced Molecular Cloning, were added to 30 μl of every third aliquot of the two gradients. The aliquots and DNA size standards were electrophoresed on a 0.4% agarose gel at 35 V overnight. From the restriction patterns on the gel, it was determined that aliquot #10 corresponded to the desired size range (15–28 kb). Next, aliquots #9, 10 and 11 (one above and one below the correct aliquot) from the two gradients were combined in a 50 ml plastic centrifuge tube and ethanol precipitated. The resulting DNA precipitate samples were combined in 50 μl of Tris-EDTA buffer (TE), which contains 10 mM of Tris-HCl and 1 mM of EDTA at pH 8.0. The absorbance was taken at $A_{260}$ and the concentration of the DNA was calculated to be 0.425 μg/μl. To verify that the correct aliquots were precipitated, 2 μg samples of DNA were electrophoresed on a 0.4% agarose gel.

Cosmid cloning vector pVK102 was also purified according to the "Large-Scale Isolation of Plasmid DNA" procedure disclosed in *Molecular Cloning* with the following modifications, due to its large size, for a 500 ml culture: 75 ml of Solution I, 150 ml of Solution II and 112.5 ml of 5 M potassium acetate. Also, an extra protein precipitation step was added. Following the isopropanol precipitation, the pellet of the 500 ml culture was resuspended in 8 ml of TE, and 6 ml of 7.5 M ammonium acetate was added. This solution was placed on ice for 20 min and then centrifuged at 16,000 rpm in a Sorvall SS 34 rotor for 20 min. The DNA was precipitated out of the supernatant with two volumes of ethanol. Due to the large size of the cosmid (23 kb) the pellets were resuspended with gentle agitation or mixed with a pipet and not vortexed throughout the procedure. A 10 μg sample of the cesium-chloride purified vector pVK102 was restricted with SalI. Complete digestion was confirmed by electrophoresing 0.5 μg of the digest on a 0.8% agarose gel. The total volume of the remaining digest was brought up to 100 μl with TE, and ethanol precipitated. The DNA was resuspended in 9 μl of TE to give a final concentration of 1 μg/μl.

The ligation of the Alcaligenes DNA into pVK102 was performed using the Stratagene Gigapack II Plus protocol (Catalog #200211, 200212, 2002123; Mar. 6, 1990). According to Stratagenes instructions, the best ligations occur with DNA concentrations of at least 200 μg/ml. Therefore, the following ligation procedures were conducted: a 1:2 ligation with 2 μg of vector and 4 μg of insert (6 μg total DNA) in 25 μl total volume, and 1:5 ligation with 2 μg of vector and 10 μg of insert (12 μg total) in 50 μl. These two ligations were incubated at 14° C. for 4 h, and then heat inactivated at 65° C. for 10 min.

The ligated vectors were packaged into heads of bacteriophage λ by following Stratagenes packaging protocol and using a culture of the E. coli strain PLK-A, which was prepared in 5 ml tryptone broth (TB) with 0.2% maltose and grown at 37° C. overnight.

Transduction procedures were performed once the DNA was packaged and a culture of E. coli strain PLK-A was grown. The following procedure was repeated for each ligation. In separate tubes, 1 μl and 10 μl of the packaged Alcaligenes DNA were added to 200 μl of the host bacteria, PLK-A. This mixture was incubated at 37° C. for 20 min. Then 1 ml Luria-Bertani medium (LB) was added to each tube and the tubes were inverted (not vortexed) and incubated at 37° C. for 1 hour. A negative control was prepared with 200 μl of the PLK-A host cells only. After the 1 hour incubation, 100 μl and the pellet of each of the two transductions were plated on LB-kanamycin (50 μg/ml) plates and grown at 37° C. overnight. Many colonies were observed on the experimental plates and none on the control plate. Eight colonies were chosen for analysis from the 1 μl packaged Alcaligenes DNA, 100 μl plate, for each ligation. Five milliliter LB-kanamycin cultures were inoculated and grown at 30° C. for 2 days. DNA minipreparations were prepared according to the Maniatis procedure, and then analyzed by agarose gel electrophoresis. A 15 μl sample (one half of the total volume) of each DNA minipreparation was digested with restriction enzyme SalI and electrophoresed on a 0.8% agarose gel. The restriction patterns showed that 88% (7 of 8) of the colonies from the 1:5 ligation had inserts compared to only 50% (4 of 8) of the colonies from the 1:2 ligation. In order to preserve the library, 5 ml of LB was added to the 1:5 ligation 10 μl packaged Alcaligenes DNA pellet plate (containing >2000 colonies). The colonies were scraped off with a sterile spatula, the LB containing the cells was pipeted into a sterile tube, and kanamycin (km, 50 μg/ml) was added. This culture was grown at 37° C. for 2 hours and then frozen in glycerol.

EXAMPLE II

Mating into Pseudomonas

Five ml LB cultures of the mobilizer HB101 (pRK2013) (kanamycin, 50 μg/ml) and the recipient P. putida ATCC 12633 were prepared. The cultures were grown at 30° C. until mid-log phase (approximately 5 hours). The donor was prepared by adding 5 ml of LB to the plate of the Alcaligenes library packaged in PLK-A containing approximately 2000 colonies. The colonies were scraped off the plate with a sterile spatula and the LB containing the cells was pipeted into a sterile 18 ml test tube. The densities of the three cultures were made equal and the mixtures for the mating procedure were prepared. Two Donor-Mobilizer-Recipient (DMR) mixtures were made in the following ratios: 3:1:1 ratio of 150 μl donor, 50 μl mobilizer and 50 μl recipient, and 1:1:1 with 50 μl of each donor, mobilizer and recipient. From each mixture 100 μl were spotted onto an LB plate, left to dry at room temperature, and grown at 30° C. overnight. Also combinations of DR, MR and D were mixed and spotted on an LB plate. The next day, the spotted mixtures were scraped off the plate with a sterile spatula and diluted into M9 salts (per liter: 6 g of $Na_2HPO_4$, 3 g of $KH_2PO_4$, 0.5 g of NaCl, 1 g of $NH_4Cl$ 1 and 10 ml of 0.01 M $CaCl_2$). The following dilutions were plated on M9-kanamycin (50 μg/ml): $10^{-1}$, $10^{-2}$, $10^{-3}$, $10^{-4}$, and $10^{-5}$, and grown at 30° C. overnight.

This mating procedure was followed for the other subcloning experiments, except prior to preparing the mating mixtures, the cultures were centrifuged for 15 seconds in a microcentrifuge and resuspended in an equal volume of LB without antibiotics. Three times the amount of the E. coli strains (compared to P. putida) was used for all of the mixtures. When plating the mated colonies, only a loopful of the spot was diluted into M9 medium, which contained 1 ml of 1 M $MgSo_4.7H_2O$ and 10 ml of 20% glucose per 1 liter of M9 salts. Then a loopful of this culture was streaked for single colonies on M9 plates (with the appropriate antibiotics), and grown at 30° C. overnight. M9 plates were prepared by adding 15 g of bacto-agar into 1 liter of the M9 medium. Single colonies were picked and screened for nitrification activity (Example V).

The minimal M9 medium selected against the E. coli donor and mobilizing strains, and the kanamycin selected for P. putida cells containing the cosmid. A total of 1500 colonies were individually picked with a toothpick and screened for nitrite production from hydroxylamine. Seventeen colonies appeared positive for nitrite production. DNA minipreparations were made from the 12 most active colonies according to the Maniatis procedure and analyzed by gel electrophoresis. The total DNA minipreparation was digested with either SalI or SalI+BglII, and electrophoresed on a 0.8% agarose gel. Seven colonies contained inserts with the same restriction patterns which were positioned in either orientation. Two plasmids, pAB9 and pAB10 which contained the same insert in opposite orientations were chosen for further study, as well as plasmid pAB16 which contained a random chromosomal insert and served as a control. FIGS. 1 and 2 show restriction maps for plasmids pAB9 and pAB10, respectively. The restriction maps were prepared by following the mapping protocols well known in the art.

EXAMPLE III

Determination of Kinetic Parameters of Nitrifying Organisms

At the beginning of the day, 5 ml LB-kanamycin (50 μg/ml) cultures of A. faecalis DSM 30030, P. putida (pAB16) and P. putida (pAB9) were prepared and grown approximately 8 hours at 30° C. with shaking. The cultures were then centrifuged at 8000 rpm in a Sorvall SS 34 rotor for 10 min, and the pellets were resuspended in 2 ml of Alcaligenes medium (per liter: 2.8 g Na citrate, 0.5 g $NH_4Cl$, 40 mg $MgSO_4.7H_2O$, 0.02 mg $CaCl_2.2H_2O$, 0.2 g $KH_2PO_4$ and 10 mg $FeSO_4.7H_2O$; pH=6.5) with ammonium chloride added to a final concentration of 500 ppm. One ml of this culture was used to inoculate 50 ml of Alcaligenes medium (with ammonium chloride, 500 ppm, and kanamycin, 30 μg/ml). The culture was incubated at 30° C. overnight.

The overnight cultures of A. faecalis DSM 30030 and P. putida (pAB9) were grown to stationary phase. They were then added to 300 ml Alcaligenes medium (with ammonium chloride, 500 ppm, and kanamycin, 30 μg/ml) in a 1 liter flask, and reincubated at 30° C. for 1 hour. At the time of harvesting, the $A_{600}$ equaled 0.081 for pAB9. The cultures were then centrifuged at 6500 rpm in a Sorvall GS 3 rotor for 15 min. The pellets were washed in an equal volume of Alcaligenes medium without ammonium chloride or kanamycin, and resuspended in the same medium. Fifty milliliters were aliquoted into each of six 250 ml flasks, and kanamycin (30 µg/ml) was added. Ammonium chloride was added to the six flasks to give final concentrations of 0, 2, 5, 10, 20 and 50 ppm of $NH_3$-N. An initial sample of 6 ml was withdrawn, and the cultures were regrown at 30° C. Samples were taken at 2.5, 4.5, 8.5 and 24 hours, and assayed for ammonia, nitrate and nitrite. The same procedure was repeated for Arthrobacter sp,. using the Arthrobacter medium (per liter: 16.9 g Na citrate, 4.7 g $(NH_4)_2SO_4$, 0.5 g $MgSO_4.7H_2O$, 0.5 mg $CaSO_4$, 8.16 g $KH_2PO_4$, 1.6 g NaOH, 0.5 g KCl, 0.5 mg $CuSO_4.5H_2O$, 0.5 mg $FeCl_3.6H_2O$ and 0.5 mg $ZnSO_4.H_2O$; at a pH of 7.0). The results are shown in Table 1.

TABLE 1

|  | Apparent $K_m$ (mg $NH_3$—N/l) | Apparent $V_{max}$ (mg $NH_3$—N/ mg protein/hour) |
|---|---|---|
| Arthrobacter sp. | 9 | 0.012 |
| A. faecalis | 10 | 0.07 |
| P. putida (pAB9) | 5 | 0.25 |

These results show that the apparent $K_m$ and the apparent $V_{max}$ of the recombinant organism are about 350% higher and about 50% lower, respectively, than those of the parent organism, A. faecalis, indicating that the recombinant organism is a more efficient nitrifier.

EXAMPLE IV

Subcloning of the hao Gene

The plasmid pAB10 (see FIG. 2) was simultaneously digested with BglII+HindIII and three restriction fragments were isolated. They were then subcloned into pSP329 (Schmidhauser and Helinski, J. Bacteriol 1985, 164, 446–455). The three fragments were BglII - HindIII (5.5 kb), HindIII - HindIII (4.6 kb) and HindIII - HindIII (5.2 kb) where the last HindIII site was located in pVK102. The large BglII - SalI (8.5 kb) fragment was not tested. The three subclones were designated. pAB21, pAB19 and pAB20, respectively. All three subclones were tested for nitrite formation from hydroxylamine and ammonia. Only plasmid pAB21 contained a DNA fragment that encoded the HAO activity, converting hydroxylamine to nitrite. The 5.5 kb fragment therefore encodes the A. faecalis hao gene. Using techniques well known in the art, a detailed restriction map of this region has been generated (see FIG. 4). Several subfragments of this region have been recloned and tested for activity. Referring to FIG. 4, DNA fragments 4, 5, 7, 8 and 10 were non-active, and DNA fragment 6 was fully active. About half of the cloned specimens of DNA fragment 9 were partially active. These results indicate that the DNA sequence encoding the hao gene is located between the BglII and PstI restriction sites, which is about 5.1 kb in length.

EXAMPLE V

Screening for Nitrification by Transformed Organisms

The following standard concentration assay was developed to determine the nitrite concentrations in test specimen. A 1 M $NaNO_2$ solution in phosphate-buffered saline (PBS; 8 g NaCl, 0.2 g KCl, 1.15 $Na_2HPO_4.7$ $H_2O$ and 0.2 g $KH_2PO_4$) was prepared and diluted with PBS to make standards with the following concentrations in mM: 500, 200, 100, 10, 1, 0.8, 0.6, 0.4, 0.2, 0.1, 0.08, 0.06, 0.04, 0.02, 0.015, 0.010, 0.005. From each dilution, 100 µl were pipeted into a well of a microtiter plate (U shaped wells), and 100 µl of nitrite color reagent were added. The color reagent was composed of 2 parts 4% sulfanilamide (Fisher) in 25% concentrated HCl and 1 part 0.08% N-(1 Naphthyl)-ethylenediamine dihydrochloride, reagent ACS (Kodak) and was prepared just prior to use. A 50 µl sample of the 100 µM dilution diluted in 0.95 ml of PBS was scanned using a Perkin-Elmer Lambda 5 UV/VIS Spectrophotometer. The maximum absorbance was recorded at $A_{540}$. For each of the remaining standards, 100 µl aliquots were read at $A_{540}$. A standard curve was created from these values.

A study was conducted to screen nitrite-producing strains in the presence of hydroxylamine and ammonia. The following strains were grown in 5 ml LB with the appropriate antibiotics at 30° C. overnight: P. putida (pAB16), P. putida (pAB9), and P. putida (pAB10) all with kanamycin (50 µg/ml); P. putida (pAB19), P. putida (pAB20) and P. putida (pAB21) all with tetracycline (75 µg/ml); and P. putida ATCC 12633 and Alcaligenes faecalis DSM 30030. The following morning the cultures were diluted 1:10 and regrown for 5 hours. The cultures were then centrifuged at 5000 rpm in a Sorvall SA 600 rotor for 10 min and resuspended in 1 ml PBS. The absorbance of a 100 µl sample from each culture in 900 µl PBS was determined at $A_{550}$. All of the cultures were diluted to a density of 0.3 with PBS. The total volume to give 0.3 is calculated by dividing 0.3 into the absorbance value. Once the densities of the cultures were equalized, they were subjected to the following hydroxylamine and ammonia assays. From each diluted culture, 50 µl were mixed with 50 µl of hydroxylamine, hydrochloride, ACS reagent (100 µg/ml, dissolved in PBS, filter sterilized; Sigma) in the well of a microtiter plate, providing 10 ppm hydroxylamine-N concentration. This mixture was incubated at 30° C. for 30 min. Controls containing "culture only" and "no cells" were prepared.

The above procedure was repeated for ammonia, except cells were diluted in a 1:10 ratio in Peptone-Meat broth (PM; per 1 liter: 5 g peptone and 3 g beef extract and at a pH of 6.5), and, instead of hydroxylamine, 50 µl of ammonium chloride (400 µg/ml in PBS, filter sterile) were added to 50 µl of each strain, providing 52 ppm ammonia-N concentration. This assay was incubated at 30° C. for 1.5 h.

After the respective incubation period, 100 µl of the color reagent (see above) were added to each well. A color change occurred within 1 min. For both assays, 100 µl of each strain were centrifuged for 2 min to pellet any remaining bacteria. Absorbances were then recorded at $A_{540}$.

The results of the nitrite assays from hydroxylamine and ammonia are shown in Table 2. All of the control strains (A. faecalis DSM 30030, P. putida ATCC 12633 and P. putida (pAB16)) accumulated nitrite at approximately 0.6 to 0.9 ppm when hydroxylamine was added to the reaction. P. putida (pAB9) and P. putida (pAB10) accumulated nitrite above 3.5 ppm. A subclone of the hao gene, pAB21, gave similar results to pAB9. The results confirm that the DNA sequence encoding the hao gene is located between the BglII and PstI restriction sites, and the result of the nitrification experiments directly from ammonia shows over 2-fold increase in nitrite production for pAB10 for the entire pathway, compared to that of the donor.

TABLE 2

| Strain | Nitrite from Hydroxylamine (ppm) | Nitrite from Ammonia (ppm) |
| --- | --- | --- |
| A. faecalis (DSM 30030) | 0.604 | 0.359 |
| P. putida (ATCC 12633) | 0.873 | — |
| P. putida (pAB16) | 0.715 | ND* |
| P. putida (pAB9) | 3.571 | 0.406 |
| P. putida (pAB10) | 4.180 | 0.912 |
| P. putida (pAB19) | 0.572 | ND |
| P. putida (pAB20) | 0.596 | ND |
| P. putida (pAB21) | 3.618 | ND |
| P. putida (pAB51) | 4.233 | 4.992 |
| Culture Only | ND | ND |
| No Cells | ND | ND |

*ND = not detected (undetectable concentration).

EXAMPLE VI

Generation of Bacterial Growth Curves

Overnight 5 ml cultures were prepared in LB of the following strains: E. coli W3110, Alcaligenes faecalis DSM 30030, P. putida (ATCC 12633), P. putida (pAB9) and P. putida (pAB10). Cultures containing pAB9 and pAB10 required kanamycin (50 µg/ml). All cultures were grown at 30° C.

The next morning, the cultures were diluted 1:100; 200 µl into 20 ml LB (plus kanamycin if necessary), in a 250 ml Erlenmeyer flask. An initial 200 µl sample was removed. The cultures were reincubated at 30° C. Every hour, 200 µl samples were taken from each culture. This resulted in a total of 8 samples over 7 hours for each culture. Immediately after sampling, the absorbances of 100 µl of the samples were read at $A_{550}$.

Figure 8:
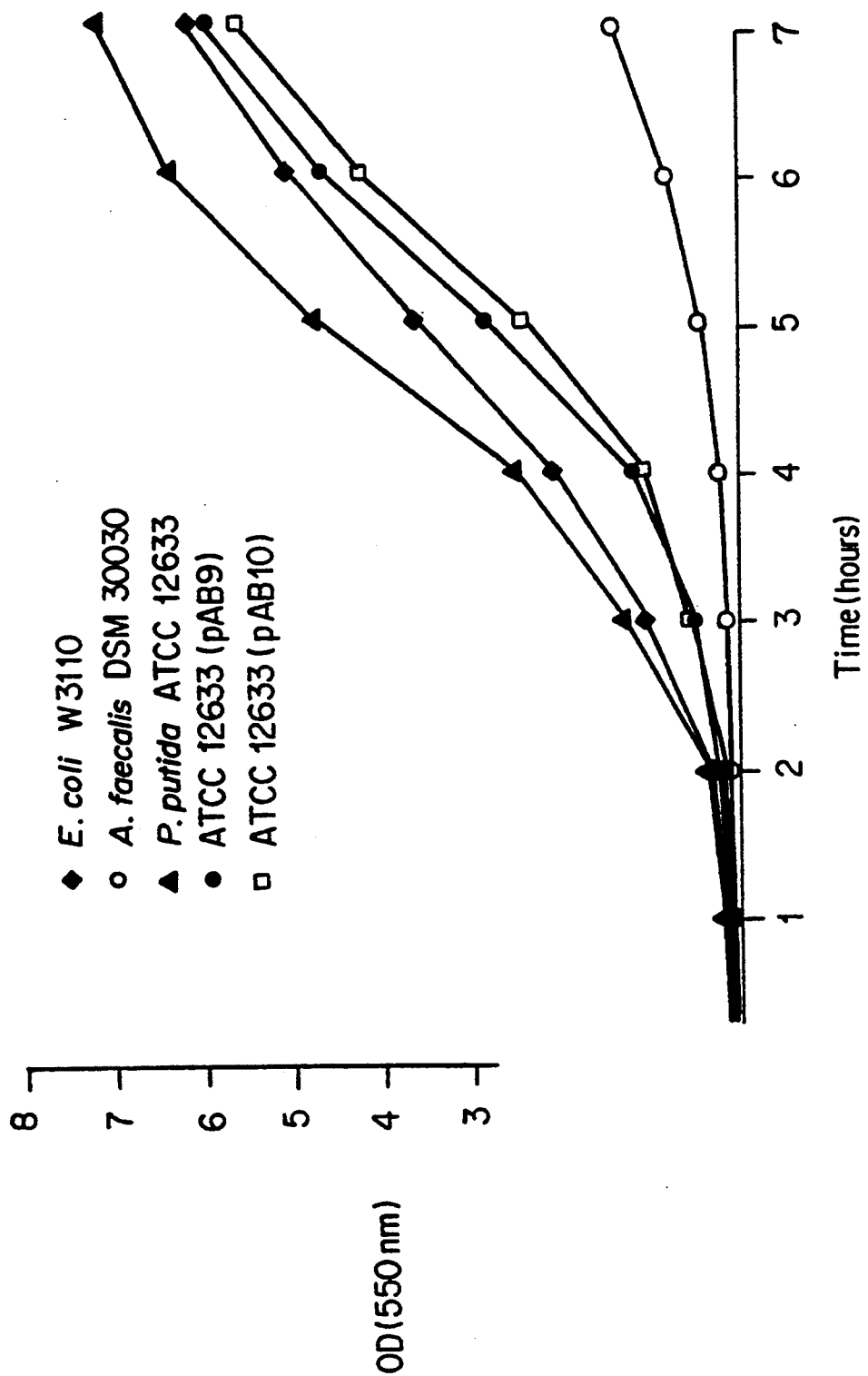
FIG. 8 is a growth curve of various microorganisms described in the invention.

A graph was generated which plots time of growth versus density of the culture (see FIG. 8). As is apparent from the figure, A. faecalis is the slowest-growing strain and P. putida ATCC 12633 has the fastest growth rate. The two recombinant organisms containing plasmids pAB9 and pAB10 have good growth rates which are achieved even in the presence of the antibiotic kanamycin, and their growth rate is over four-fold faster than that of the donor organism A. faecalis.

EXAMPLE VII

(A) Degradation of TCE

Cultures were prepared (in duplicate) in 5 ml of LB, of the following strains: E. coli W3110, Alcaligenes faecalis (DSM 30030), P. putida (ATCC 12633), P. putida (pAB9), P. putida (pAB10) and P. putida (pAB16). Cultures containing pAB9, pAB10 and pAB16 required kanamycin (50 µg/ml). These cultures were inoculated from frozen glycerols and grown at 30° C. overnight.

The next morning the cultures were diluted 1:10 in a 250 ml Erlenmeyer flask; 5 ml into 45 ml PM, and kanamycin was added, when needed. The cultures were reincubated at 30° C. for 5 hours. At that time the parent strains had reached the log phase (E. coli W3110, A. faecalis and P. putida). The density of P. putida (pAB16) was less than the parent strain's, and the densities of the pAB9- and pAB10-containing strains were even less. The 50 ml cultures were split into two 50 ml centrifuge tubes, and centrifuged in an SA 600 rotor at 7500 rpm for 10 min. The two pellets for each strain were resuspended in a total of 10 ml of PBS. The absorbance of a 100 µl sample from each strain was determined at $A_{550}$. The volume of each strain required to achieve a density of $A_{550}=0.3$ was calculated and the corresponding amount of PBS was added. Each bacterial suspension was then transferred to a Wheaton "400" serum bottle (125 ml capacity, 20 mm mouth, Mfr#223748). The bottles were capped with Wheaton aluminum caps (tear out center disc, Mfr#224223) with 20 mm natural rubber teflon-lined septa (teflon side to the medium) using Wheatons Manual Crimper (Mfr#224303). A stock solution of trichloroethylene (TCE) was prepared by completely filling a serum bottle with sterile water, capping it without trapping any air bubbles and adding 1 ml of TCE (Aldrich) with a syringe. The bottle was mixed vigorously and stored at room temperature overnight. The following morning, as expected, a layer of TCE still remained on the bottom of the bottle, but the water was saturated with TCE. From this TCE stock a 1:50 dilution was made in each bacterial suspension, resulting in a TCE concentration of approximately 10 ppm per bottle. Finally, 5 cc of oxygen were added to each bottle, and the bottles were incubated at 30° C. overnight.

The next morning the cells were harvested. P. putida (pAB10) showed some white precipitate in the medium, strains containing pAB9 and pAB16 had less, and the parent strains had none. The bottles were then uncapped using Wheatons Hand-Operated Decapper (Mfr#224373) and 5 ml of each strain were pipeted into a vial containing 100 µl of 1 M HCl to inactivate any remaining bacteria. The vials were capped with teflon-coated seals, without trapping any air bubbles. The samples were analyzed for TCE content and nitrite production. Hachs procedure for assaying nitrite (see Example I) was followed. The results are shown in Table 3.

TABLE 3

| Strain | TCE remaining (ppm) |
| --- | --- |
| E. coli | 9.1 |
| P. putida | 9.2 |
| A. faecalis | 7.6 |
| P. putida (pAB9) | 3.7 |
| P. putida (pAB10) | 3.5 |

Only pAB9 and pAB10 were shown to produce nitrite, an indication of AMO activity. Corresponding to these results, our analyses of volatile organic compounds showed that these two samples had degraded over 60% of the added TCE, while the parent strain A. faecalis had degraded only 24% of the TCE over the same time interval.

(B) Rate of TCE Degradation

Cultures of P. putida (pAB9) and P. putida (pAB10) were prepared as previously described. These cultures were grown at 30° C. for 8 hours. The 5 ml cultures were then added to 40 ml LB (and kanamycin), in a 250 ml Erlenmeyer flask. The cultures were reincubated at 30° C. for 11 h. Then the cultures were diluted 1:10 in a 2-liter Erlenmeyer flask; 40 ml into 360 ml PM broth (and kanamycin), and regrown at 30° C. for 5 hours. The 400 ml cultures were divided into two 400 ml centrifuge tubes, and centrifuged in a Sorvall GS3 rotor at 5000 rpm for 20 min. The two pellets for each strain were resuspended in a total of 80 ml PBS. The densities of the two strains were adjusted to $A_{550}=0.3$ with PBS. Six bottles with 50 ml of bacterial suspension were set up for each strain, and capped. To each bottle, 1 ml of TCE was added from the stock bottle. Finally, 5 cc of oxygen were added to each bottle. Five bottles for each strain were incubated at 30° C. The cells of the sixth bottle were harvested as the initial sample. The cells of one bottle were harvested at 1.5, 3.0, 4.5, 6.0 and 24 hours, for each strain. The samples were analyzed for TCE degradation and nitrite production.

The most TCE degradation occurred in the first 1.5 hours of incubation for pAB9 and pAB10, up to a maximum initial rate of 1.4 nmol TCE/min per mg of protein.

(C) TCE Degradation in the Presence of 1-Allyl-2-thiourea

This experiment was conducted with P. putida (pAB10) to determine the effect of 1-Allyl-2-thiourea (ATU) on the degradation of TCE. ATU is a specific, non-competitive inhibitor of AMO. The protocol described in section (A) was repeated in duplicate with the following changes. Cultures were prepared in 25 ml of LB and kanamycin (50 µg/ml) in 250 ml flasks. These cultures were inoculated from frozen glycerols and grown at 30° C. overnight. The following morning four flasks of the diluted overnight culture were set up for each strain. The cultures were diluted 1:10, 5 ml into 45 ml PM broth and reincubated at 30° C. for 4 hours. At that time, 1 ml of freshly prepared 25 mM ATU (dissolved in water, filter sterilized) was added to two flasks of each strain, for a final concentration of 500 µM. All of the cultures were incubated at 30° C. for 20 min before centrifugation.

The volumes for each sample were adjusted to a density of $A_{550}=0.3$, and ATU was added to the same two cultures of each strain to a final concentration of 50 µM. TCE (10 ppm final concentration) and 5 cc of oxygen were added to each bottle. The bottles were incubated at 30° C. for 1.5 hours. Samples were then removed from the bottles and analyzed for TCE content and nitrite production. The bottles were recapped and incubated at 30° C. overnight.

The next morning the cells were harvested. All of the cultures showed some white precipitate in the medium. The samples were analyzed for TCE content and nitrite production. The results are shown in Table 4.

TABLE 4

| Incubation Time (hour) | TCE Remaining (ppm) | | Nitrite Produced (ppm) | |
|---|---|---|---|---|
| | +ATU | −ATU | +ATU | −ATU |
| 1.5 | 9.3 | 6.1 | 0.9 | 2.7 |
| 16.0 | 7.4 | 5.4 | 1.1 | 3.1 |

The results demonstrate that TCE degradation was inhibited in the presence of 50 µM ATU. Nitrite production was concurrently reduced, which was expected. These data suggest that the enzyme AMO is involved in the TCE degradation.

EXAMPLE VIII

Localization of the amo Gene

A transposon mutagenesis experiment was conducted to determine the location of the amo gene on pAB10. This experiment was based on the premise that any randomly obtained transposon insertion which would lead to inactivation of the nitrification pathway would be located in either the amo or hao genes. Since the position of the hao gene is already known, any remaining insertions would most likely have occurred in the amo gene.

The cosmid pAB10 was transformed into E. coli strain DH5α (ColiE1::Tn5G) (gentamicin$^R$, 30 mg/l) using the Hanahan procedure. The transformation mixture was allowed to incubate at 37° C. for 4 hours prior to plating onto selective medium in order to allow the transposon to transpose and to express the Gm$^R$ gene. The mixture was then plated onto LB-Km-Gm plates and incubated at 37° overnight. Approximately 300 colonies were obtained. In order to gain a reasonable number of transposon insertions in the nitrification genes (greater than one insert per 1000 bp), it was estimated that a minimum of 6000 colonies were needed. The protocol was therefore scaled up twenty-fold and the necessary number of colonies was obtained.

The colonies were pooled and batch-mated into E. coli CF800(polA−, Rif$^R$) using HB101 (pRK2013) as the mobilizer. The procedure was analogous to the one described in example II. The choice of CF800 is important in that the plasmid ColiE1::Tn5G cannot replicate in a polA− host. The mating mixture was plated for single colonies on LB-Gm plates containing either 40 mg/l or 100 mg/l rifampicin (Rif). Both concentrations of Rif worked equally well. The only colonies which could grow on the selective plates were CF800 hosts containing copies of pB10 with Tn5G insertions, which rendered the plasmids Gm$^R$. Approximately 3000 such colonies were obtained.

A mixture of these colonies was then batch-mated into P. putida using HB101 (pRK2013) as the mobilizer. Single colonies were selected on LB-Cm (chloramphenicol, 34 mg/l)-Gm plates. Contrary to E. coli, P. putida is not sensitive to Cm at this concentration.

Approximately 500 colonies were tested for their ability to convert ammonia to nitrite. Several negative colonies were identified and retested. Twenty confirmed colonies unable to convert ammonia to nitrite were chosen and tested for HAO activity. In the hydroxylamine assay, most colonies showed some deficiency in HAO activity. Only three colonies were fully active in converting hydroxylamine to nitrite and several were partially active.

DNA minipreps were prepared from all 20 negative colonies and digested with BglII and HindIII endonucleases to locate the transposon insertions. This digestion separates the 5.5 kb BglII - HindIII fragment (containing HAO), and the 4.6 kb HindIII fragment and the 5.2 kb HindIII fragment. The 8.5 kb SalI - BglII fragment which represents the remaining insert in pAB10 is included as part of the large vector fragment. After electrophoresis on a 0.8 agarose gel, the data showed that all 20 isolates contained a Tn5G insertion in pAB10. In no case was an insertion found in either the 4.6 kb or 5.2 kb HindIII DNA fragments, indicating that the two fragments do not contain the amo gene.

These results indicate that all Tn5G insertions leading to ammonia oxidation deficiency are located in either the 5.5 kb hao-containing DNA fragment or in the adjacent 8.5 kb SalI - BglII DNA fragment. Since the 5.5 kb hao-containing segment did not exhibit any AMO activity, as demonstrated in Example V, the amo gene is most likely located on the 8.5 kb SalI - BglII fragment. The fact that hao deficiency was observed in numerous instances where the Tn5G insertion was not located in the hao structural gene suggests that this gene is part of an operon, possibly with amo.

EXAMPLE IX

Activity Determination of the Cloned amo Gene

Plasmid pAB10 was digested with restriction enzymes BglII and SalI, and electrophoresed on a 0.7% agarose gel. The 8.5 kb BglII - SalI DNA fragment was excised and purified using the Geneclean kit (Bio101). The DNA fragment was then ligated into endonucleases BglII+SalI—digested vectors p Bluescript ® II KS and SK, which are available from Stratagene, and transformed into E. coli host XL1-Blue, also available from Stratagene. The plasmids containing the inserts in p Bluescript ®II KS and SK were designated pAB38 and pAB39, respectively. A restriction map of pAB38 is shown in FIG. 6.

In order to further define the location of the amo gene, subclones of pAB38 and pAB39 were prepared. The vectors were digested with restriction enzyme ApaI and self-religated, giving rise to corresponding vectors pAB42(KS) and pAB43(SK). Each of the new vectors contains a subclone of the 8.5 kb region of approximately 3 kb which covers the region between the ApaI restriction site and the BglII restriction site directly adjacent to the hao-containing DNA fragment.

An assay for the conversion of ammonia to hydroxylamine ($NH_2OH$) was then developed and the four vectors were tested for AMO activity. The hydroxylamine assay was based on the one published by Magee and Burris (*Amer. J. Bot.* 1954, 41, 772–782). Standards were prepared containing the following concentrations of $NH_2OH$-N: 200 ppm, 20 ppm, 2 ppm, 0.2 ppm, 0.02 ppm and 0.002 ppm. In a large test tube, 2 ml of standard was mixed with 1 ml of 1 M $Na_2CO_3$ (in $H_2O$) and 1 ml of 1% 8-hydroxyquinoline (in 100% ethanol). All samples were incubated at room temperature with agitation for 80 min. At the beginning of the incubation period, all solutions turned bright yellow. Over the next few minutes, the samples containing the two highest concentrations of $NH_2OH$-N began to turn green. After 80 min, the A of all samples was determined at the wavelength (700 nm) at which maximum absorbance occurred.

Bacterial cultures were prepared for the hydroxylamine assay as follows: DH5α and DH5α(pAB31) (5.5 kb HAO fragment in pBluescript ® II SK) as negative controls, XL1-Blue(pAB38), XL1- Blue(pAB39), DH5α(pAB42) and DH5α(pAB43) were grown in 5 ml overnight cultures in LB broth. Ampicillin (Ap) was added to the growth medium as required. The next morning, the cultures were diluted 1:10 into 5 ml LB(+Ap), and incubated at 37° C. for 3 hours. The cells were then harvested by centrifugation (5000 rpm, 10 min) and the cells were resuspended in 1 ml of PBS. The absorbance of a 100 ml sample from each culture in 900 ml PBS was determined at $A_{500}$. All of the cultures were diluted to a density of 0.15 with PBS. One ml of cells and 1 ml of $NH_4Cl$ (400 mg/ml in PBS) were combined in a large culture tube and incubated at 37° C. for 1 hour. The hydroxylamine assay was then performed as described above using a 52 ppm concentration of $NH_3$-N and the absorbance at $A_{690}$ was determined. The results, shown in Table 5, indicate that all cultures containing the putative amo gene (pAB38, pAB39, pAB42, and pAB43) produce approximately 2 times more hydroxylamine than the control cultures. Therefore, it is believed that the amo gene is located on the 3 kb ApaI - BglII fragment (3) in FIG. 6. The sequence of the entire 3 kb fragment appears in FIG. 9. This fragment is directly adjacent to the hao-containing region. Since the fragment is active in either orientation, it is likely that the amo gene is transcribed off its own promoter.

TABLE 5

| Strain | $A_{690}$ | $NH_2OH$—N Concentration (ppm) |
|---|---|---|
| DH52a | 0.024 | 0.034 |
| DH52 (pAB31) | 0.024 | 0.034 |
| XL1-Blue (pAB38) | 0.046 | 0.064 |
| XL1-Blue (pAB39) | 0.044 | 0.062 |
| DH5a (pAB42) | 0.052 | 0.073 |
| DH5a (pAB43) | 0.053 | 0.074 |

EXAMPLE X

Construction of Nitrification Vector pAB51

A nitrification vector which contains the amo and hao genes in their original orientation on a continuous DNA fragment was constructed. Initially, the 100 bp PstI - BglII fragment from vector pAB42 (3.0 kb amo—encoding insert) was deleted in order not to create a duplication of this region later in the strategy by digesting pAB38 with restriction enzymes ApaI+PstI. The digest DNA fragments were electrophoresed on a 0.7% agarose gel and the 2.9 kb ApaI - PstI segment was isolated and purified using the Geneclean kit. This fragment was then subcloned into ApaI+PstI—digested pBluescript ® II KS, giving rise to plasmid pAB44.

The construct was then moved into pSP329. Plasmid pAB44 was digested with ApaI and the restriction site was made blunt-ended with T4 DNA polymerase. The vector was then cut with XbaI. The 2.9 kb insert fragment was purified from agarose using the Geneclean kit. The vector pSP329 was prepared by digesting with PstI and blunt-ending the restriction site with T4 DNA polymerase. The vector was then digested with XbaI. The vector and insert fragments were joined via the XbaI restriction site and a novel joint created by the blunt-ended ApaI and PstI restriction sites; resulting in plasmid pAB47.

The last step was to insert the PstI segment containing the hao region from pAB9 into pAB47. The plasmid pAB9 was digested with PstI and the 5.1 kb hao-encoding DNA fragment was isolated. This insert was then ligated into PstI-digested pAB47. The ligation mixture was transformed into E. coli DH5α and 15 colonies were obtained. DNA minipreps were prepared, and the DNA samples were digested with BamHI+HindIII endonucleases and analyzed on a 0.7% agarose gel. One construct was obtained which had a tandem insertion of the PstI fragment, designated pAB49. This plasmid was digested with BglII and self-religated. One of the tandem inserts was thereby deleted, resulting in the desired 8.1 kb DNA construct. This plasmid consisted of an hao-containing fragment (PstI-BglII) and an amo-containing fragment (BglII-ApaI) with the BglII site serving as the junction between the two genetic regions. This final vector was designated pAB51, and a restriction map of the vector was constructed as shown in FIG. 7.

pAB51 was transferred into P. putida using the mating procedure described in Example II. Three colonies containing pAB51 were picked and assayed for nitrite production from ammonia and from hydroxylamine as described in Example V.

P. putida(pAB51) accumulated nitrite from hydroxylamine at 4.233 ppm and from ammonia at 4.992 ppm.

The resulting nitrite concentrations are about 700% and 1400%, respectively, of the concentration obtained by the donor, A. faecalis DSM 30030, as stated in Example V.

As can be seen from the above examples, the transformed microorganisms of the present invention efficiently consume or convert ammonia and other chemicals from the media that contain ammonia and/or other substrate chemicals as well as organic carbon and other organic compounds, and are fast growers that compete well with other natural microorganisms.

The present transformed microorganisms that contain the hao and amo genes are suitable for the use in bioremediation and/or oxidative-conversion of ammonia and other compounds such as halogenated hydrocarbons, amines, aliphatic hydrocarbons, benzene, sulfide and the like. The transformed microorganisms can also be employed to oxidatively convert, for example, amines, aliphatic hydrocarbons, benzene and sulfides to provide hydroxylamines, aliphatic alcohols, phenol and sulfoxides, respectively, which are commercially valuable products.

We claim:

1. A plasmid for transformation of a host microorganism, said plasmid comprising a polydeoxyribonucleotide insert obtained from an *Alcaligenes faecalis* donor, wherein said polydeoxyribonucleotide insert codes for ammonia monooxygenase and hydroxylamine oxidoreductase as found in the microorganism with the accession number NRRLB-18893.

2. The plasmid of claim 1, wherein said polydeoxyribonucleotide insert which codes for hydroxylamine oxidoreductase has a nucleotide sequence as set forth in SEQ ID NO: 1.

3. The plasmid of claim 1, wherein said polydeoxyribonucleotide insert which codes for ammonia monooxygenase has a nucleotide sequence as set forth in SEQ ID NO: 2.

4. The plasmid of claim 1, wherein said plasmid further comprises an expression promoter for expression of the genes on said polydeoxyribonucleotide insert which code for ammonia monooxygenase and hydroxylamine oxidoreductase.

5. The plasmid of claim 1, wherein said polydeoxyribonucleotide insert comprises 23,000 nucleotide base pairs, wherein both terminal ends of said polydeoxyribonucleotide insert are SalI endonuclease restriction sites.

6. The plasmid of claim 1, wherein said polydeoxyribonucleotide insert comprises 8,100 nucleotide base pairs and wherein one terminal end of said polydeoxyribonucleotide insert is the restriction site of the ApaI endonuclease and the other terminal end is the restriction site of the PstI endonuclease.

7. The plasmid of claim 1, wherein said polydeoxyribonucleotide insert which codes for hydroxylamine oxidoreductase comprises 5,100 nucleotide base pairs, wherein one terminal end is the restriction site of the PstI endonuclease and the other terminal end is the restriction site of the BglII endonuclease.

8. The plasmid of claim 1, wherein said polydeoxyribonucleotide insert which codes for ammonia monooxygenase comprises 3,000 nucleotide base pairs, wherein one terminal end is the restriction site of the ApaI endonuclease and the other terminal end which is the restriction site of the BglII endonuclease.

9. A transformed microorganism containing at least one copy of the plasmid of claim 1.

10. The transformed microorganism of claim 9, wherein said plasmid further comprises an expression promoter for expression of the genes on said polydeoxyribonucleotide insert which code for ammonia monooxygenase and hydroxylamine oxidoreductase.

11. The transformed microorganism of claim 9, wherein said host microorganism is selected from the group consisting of Pseudomonas, Paracoccus, Thiobacillus, and Rhodopseudomonas.

12. The transformed microorganism of claim 9, wherein said transformant microorganism has deposit number NRRL B-18893.

13. A plasmid for transformation of a host microorganism, said plasmid comprising a polydeoxyribonucleotide insert obtained from an *Alcaligenes faecalis* donor, wherein said polydeoxyribonucleotide insert codes for hydroxylamine oxidoreductase as found in the microorganism with the accession number NRRLB-18893.

14. The plasmid of claim 13, wherein said polydeoxyribonucleotide insert which codes for hydroxylamine oxidoreductase has a nucleotide sequence as set forth in SEQ ID NO: 1.

15. A plasmid for transformation of a host microorganism, said plasmid comprising a polydeoxyribonucleotide insert obtained from an *Alcaligenes faecalis* donor, wherein said polydeoxyribonucleotide insert codes for ammonia monooxygenase as found in the microorganism with the accession number NRRLB-18893.

16. The plasmid of claim 13, wherein said polydeoxyribonucleotide insert which codes for ammonia monooxygenase has a nucleotide sequence as set forth in SEQ ID NO: 2.

* * * * *